(12) United States Patent
Micheels et al.

(10) Patent No.: US 10,060,849 B2
(45) Date of Patent: Aug. 28, 2018

(54) OPTICAL ANALYZER FOR IDENTIFICATION OF MATERIALS USING TRANSMISSION SPECTROSCOPY

(71) Applicant: Innovative Science Tools, Inc., Concord, MA (US)

(72) Inventors: Ronald H Micheels, Concord, MA (US); Don J Lee, Concord, MA (US)

(73) Assignee: Innovative Science Tools, Inc., Concord, MA (US)

( * ) Notice: Subject to any disclaimer, the term of this patent is extended or adjusted under 35 U.S.C. 154(b) by 59 days.

(21) Appl. No.: 15/046,850

(22) Filed: Feb. 18, 2016

(65) Prior Publication Data

US 2016/0161402 A1      Jun. 9, 2016

Related U.S. Application Data

(62) Division of application No. 13/836,627, filed on Mar. 15, 2013, now Pat. No. 9,297,749.

(Continued)

(51) Int. Cl.
*G01J 3/00* (2006.01)
*G01N 21/359* (2014.01)
(Continued)

(52) U.S. Cl.
CPC .......... *G01N 21/359* (2013.01); *G01J 3/0205* (2013.01); *G01J 3/0216* (2013.01);
(Continued)

(58) Field of Classification Search
CPC ....... G01N 21/359; G01N 2201/06153; G01N 2201/0627
See application file for complete search history.

(56) References Cited

U.S. PATENT DOCUMENTS

| 4,379,233 | A | * | 4/1983 | Rosenthal | G01J 3/10 250/223 R |
| 5,347,433 | A | * | 9/1994 | Sedlmayr | G02B 5/285 362/268 |
| 5,473,408 | A | * | 12/1995 | Hoffman | G02B 27/09 355/53 |
| 5,813,403 | A | * | 9/1998 | Soller | A61B 5/0075 600/310 |
| 6,122,042 | A | * | 9/2000 | Wunderman | A61B 1/05 356/343 |

(Continued)

OTHER PUBLICATIONS

Micheels, Ronald. Development of Non-Invasive Deep Tissue pH Sensor. Pole Star Technologies Inc Sudbury MA, 1995.*

*Primary Examiner* — Tri Ton
*Assistant Examiner* — Rufus Phillips
(74) *Attorney, Agent, or Firm* — Clocktower Law; Erik J. Heels; Michael A. Bartley

(57) ABSTRACT

A device and method for identifying solid and liquid materials use near-infrared transmission spectroscopy combined with multivariate calibration methods for analysis of the spectral data. Near-infrared transmission spectroscopy is employed within either the 700-1100 nm or the 900-1700 nm wavelength range to identify solid or liquid materials and determine whether they match specific known materials. Uses include identifying solid (including powdered) and liquid materials with a fast measurement cycle time of about 2 to 15 seconds and with a method that requires no sample preparation, as well as quantitative analysis to determine the concentration of one or more chemical components in a solid or liquid sample that consists of a mixture of components. A primary application of such analysis includes detection of counterfeit drug tablets, capsules and liquid medications.

1 Claim, 28 Drawing Sheets

Related U.S. Application Data

(60) Provisional application No. 61/685,908, filed on Mar. 27, 2012.

(51) Int. Cl.
*G01N 21/3563* (2014.01)
*G01N 21/3577* (2014.01)
*G01J 3/10* (2006.01)
*G01J 3/02* (2006.01)
*G01J 3/42* (2006.01)
*G01N 21/95* (2006.01)

(52) U.S. Cl.
CPC ............ *G01J 3/0218* (2013.01); *G01J 3/10* (2013.01); *G01J 3/42* (2013.01); *G01N 21/3563* (2013.01); *G01N 21/3577* (2013.01); *G01N 21/9508* (2013.01); *G01N 2201/0627* (2013.01); *G01N 2201/0631* (2013.01); *G01N 2201/06153* (2013.01)

(56) References Cited

U.S. PATENT DOCUMENTS

| | | | | |
|---|---|---|---|---|
| 6,450,664 | B1* | 9/2002 | Kelly | F21V 5/045 |
| | | | | 362/218 |
| 6,741,875 | B1* | 5/2004 | Pawluczyk | A61B 5/14532 |
| | | | | 250/339.05 |
| 7,133,710 | B2* | 11/2006 | Acosta | A61B 5/0075 |
| | | | | 600/316 |
| 7,724,436 | B2* | 5/2010 | Magarill | G03B 21/006 |
| | | | | 359/618 |
| 2002/0105650 | A1* | 8/2002 | Stuttard | G01N 21/0303 |
| | | | | 356/437 |
| 2004/0223342 | A1* | 11/2004 | Klipstein | G01J 3/10 |
| | | | | 362/555 |
| 2010/0010325 | A1* | 1/2010 | Ridder | A61B 5/0075 |
| | | | | 600/310 |
| 2012/0078473 | A1* | 3/2012 | Ridder | A61B 5/0071 |
| | | | | 701/45 |

* cited by examiner

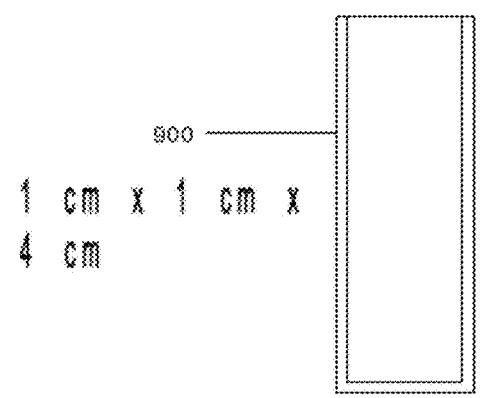
1 cm x 1 cm x 4 cm
900
Fig. 9B side
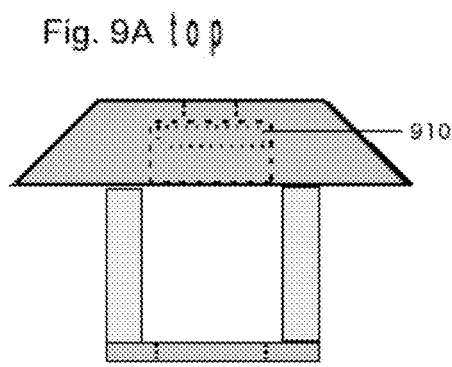
Fig. 9A top
910
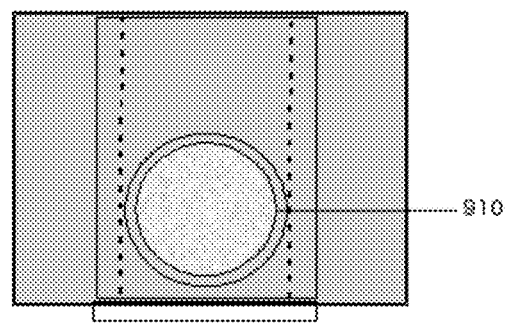
Fig. 9C front
910

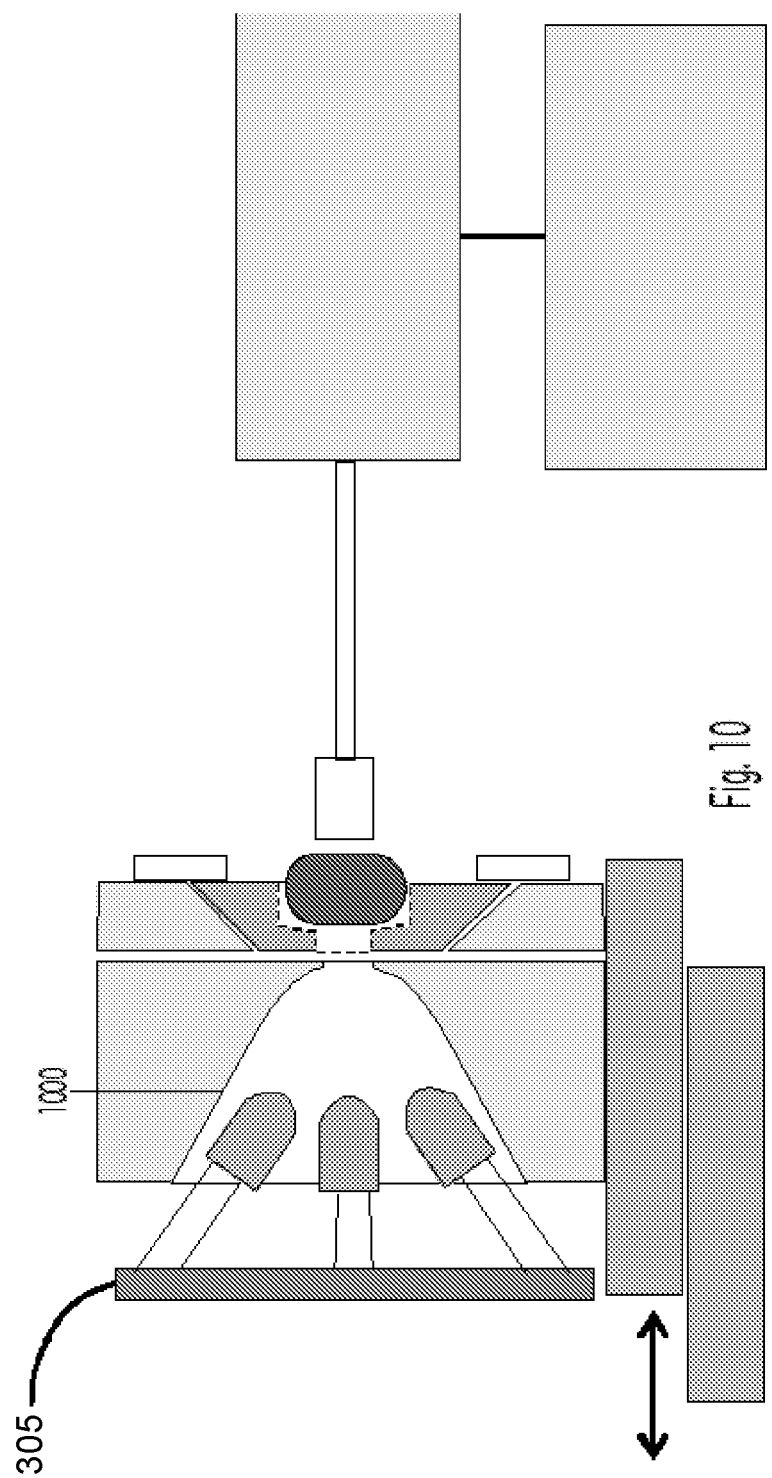

OPTICAL ANALYZER FOR IDENTIFICATION OF MATERIALS USING TRANSMISSION SPECTROSCOPY

CROSS-REFERENCE TO RELATED APPLICATIONS

This utility patent application is a division of U.S. patent application Ser. No. 13/836,627, filed Mar. 15, 2013, titled "OPTICAL ANALYZER FOR IDENTIFICATION OF MATERIALS USING TRANSMISSION SPECTROSCOPY", naming inventors Ronald H. Micheels and Don J. Lee, which claims priority from U.S. provisional patent application Ser. No. 61/685,908, filed Mar. 27, 2012, titled "Optical analyzer for identification of materials" in the name of Ronald H. Micheels and Don J. Lee.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. Copyright 2016, Innovative Science Tools, Inc.

BACKGROUND

Field of Technology

The disclosure relates to both a device and a method for identifying solid and liquid materials using near-infrared transmission spectroscopy combined with multivariate calibration methods for analyzing the near-infrared spectra. One important application of the device and method is the detection of counterfeit drug tablets and capsules.

Background

Six optical spectroscopic devices/methods that have been previously developed include: 1) light-emitting diode (LED) based spectrometer analyzers operating in the short wavelength 600-1100 nm region of the near-infrared range that use modulated LEDs; 2) Fourier-transform near-infrared spectrometers; 3) diffraction grating based near-infrared spectrometer systems (desktop size instruments that do not employ LEDs to measure the spectrum) that operate in the 800-2500 nm range (and also portable spectrometers operating in the same near-infrared range); 4) tunable acousto-optic based near-infrared spectrometers; 5) Hadamard transform based near-infrared spectrometers; and 6) laser-Raman spectrometers. The existing LED near-infrared spectrometers have been used for quantitative analysis of agricultural, fuel, and paper products. Existing Fourier-transform and single detector diffraction grating near-infrared spectrometers have been used for analysis of pharmaceutical tablets including analysis for identification of counterfeit drugs as well as other types of material identification and analysis. Existing tunable acousto-optic filter based near-infrared spectrometers could be used for identification of counterfeit drugs. An existing Hadamard transform spectrometer has been used for identification of counterfeit drugs and identification of polymers and other materials. The laser-Raman spectrometers, which have been used for drug, polymer, and general chemical identification, are usually based on a diffraction grating spectrometer with a Si-CCD of InGaAs array detection with single wavelength laser excitation at 785 or 1064 nm. Fourier-transform based laser Raman spectrometers are also available and have been used for similar applications.

The LED spectrometers described in the literature include both handheld and desktop size devices that have been used for analyzing gasoline and other petroleum fuels to measure parameters such as octane rating, and also to analyze grain and meat samples for water, fat and protein content, and also paper samples for water. In addition to operating in the 600-1050 nm wavelength range, the existing LED spectrometers use 31 or 32 LED light sources, and a wavelength filtering means consisting of either narrow bandpass interference filters associated with each LED and/or with narrow bandpass filtering of the light reaching the sample from each LED by transmission through a slit and reflection off of a diffraction grating. The existing commercial LED spectrometers employ Si photodiode detectors. Compared to the other optical spectroscopic devices, the existing LED based spectrometers have much lower spectral resolution with only 32 wavelength points compared to 512 or more points for the other technologies.

The identification of chemical components in pharmaceutical tablets and capsules and identification of counterfeit tablets and capsules has been reported using near-infrared transmission spectroscopy, where light is transmitted all the way through the tablet or capsule, with larger desktop size Fourier-transform near-infrared spectrometers and desktop size diffraction grating based near-infrared spectrometers that employ single element photodiode detectors. These spectrometers all employ a tungsten-halogen light source emitting over a wide wavelength range and measure transmission spectra by filtering the light either with a diffraction grating based monochromator, or a Michelson interferometer. These desktop instruments have a disadvantage in both high cost (about $50,000) and large size/weight relative to the new system described herein, which would greatly limit their application in testing for counterfeit drugs at drug distribution centers in developing countries. The identification of counterfeit drug tablets and capsules has also been reported with commercially available portable spectrometers including near-infrared diffraction grating array detector, near-infrared Hadamard transform, and laser-Raman spectrometers which all operate only in a reflection sampling mode. These latter spectrometers have a high cost of about $30,000-$45,000. Sampling by reflection is much less desirable than sampling by transmission because transmission sampling measures the average composition of the major portion of the entire volume of a drug tablet or capsule, while reflection sampling only sees an outer portion of the tablet/capsule that is less than 1 mm deep, and just on one side. Drug tablets are known to have substantial inhomogeneity in the distribution of active ingredients over distances on the order of 1 mm. In cases of tablets with coatings, the coatings must be removed by abrasion or cutting before analysis using surface reflection sampling. The tunable acousto-optic spectrometers have not been used for counterfeit drug identification and also have a high cost greater than $30,000.

A commercially available wet chemical test kit has been developed by the World Health Organization for testing the authenticity of drugs. To analyze tablets or capsules with this wet chemical test kit it is necessary to dissolve the sample tablet/capsule in water and then add one or more chemical reagents or then to perform a thin layer chromatography step, which are all time consuming and destructive processes (taking over 10 minutes per measurement) which consumes chemical reagents. This kit has a price of about $5,000. and a reagent kit replacement cost of $1,500 (good for 1,000 tests).

The device disclosed herein can be comparably priced to this wet chemical test kit, but has major advantages including an analysis time of about 10 to 15 seconds, and no required reagents or sample preparation.

It is also not obvious, based on existing literature, that a low-cost miniature diffraction grating, array detector near-infrared (NIR) spectrometer that operates over the 650-1100 nm wavelength range (with signal/noise of about 3000:1, and spectral resolution of 1.5 nm, with a measurement time of 15 seconds or less) would have sufficient signal/noise and detection sensitivity to measure transmission spectra through drug tablet and capsule samples and other materials (materials with an optical attenuation in the range of ×100 to ×10,000) with sufficient quality to determine the authenticity of these tablet and capsule samples or to identify the materials. Typical drug tablet and capsule samples have a high level of optical attenuation for light transmitted through the entire tablet/capsule thickness that is on the order of $10^4$. Previously, only desktop sized Fourier Transform NIR spectrometers and scanned diffraction grating NIR spectrometers with much higher price and with much higher signal/noise than the miniature diffraction grating/Si-array detector spectrometers) have been used for NIR spectroscopic drug tablet/capsule authentication using transmission sampling. These larger and more expensive spectrometers employ single element InGaAs detectors (as opposed to Si based linear array detectors) that have much higher signal/noise on the order of 20,000 to 50,000:1 relative to the miniature array detector spectrometers which have signal/noise rations on the order of 500:1 to 3,000:1. Also, the desktop single detector NIR spectrometers operate over a wider 800-2500 nm NIR spectral range as opposed to the 650-1100 nm range of the low-cost miniature diffraction grating spectrometers with Si based array detectors. For less attenuating samples such as nonscattering (clear) liquid samples measured by transmission and powder samples measured by diffuse reflectance, diffraction grating Si-array detector spectrometers have been used for materials identification, but this has not been done with the ultra-miniature spectrometers that have become recently available. These ultra-miniature spectrometers have a very small size as defined by a spectrometer polychromator focal length of ≤40 mm and spectrometer module enclosure sizes of ≤7.5 cm×5 cm×2.5 cm. As the size of a diffraction grating Si-array detector spectrometer module (operating within the 700-1100 nm range) decreases, the spectral background noise from stray scattered light, arising from light scattering inside the spectrometer enclosure, increases and also the spectral resolution decreases. As a result of these latter considerations, it is not obvious that a smaller spectrometer with lower signal/noise and spectral resolution will also be capable of such material identification with good accuracy (i.e. accuracy of greater the 90%).

BRIEF SUMMARY

A primary purpose disclosed herein is to identify solid (including powdered) and liquid materials with a fast measurement cycle time of about 2 to 15 seconds and with a method that requires no sample preparation. An alternative purpose is quantitative analysis, where the goal is to determine the concentration of one or more chemical components in a solid or liquid sample that consists of a mixture of components. Examples of material identification that such an analyzer could be used for include: 1) providing identification analysis of pharmaceutical tablets, capsules, or liquids to determine whether they are counterfeit or of the authentic type and brand stated on the packaging from which the medication was purchased in, or quality control of finished drug products including their raw materials and ingredients, both with the capability of sampling all the way through the entire thickness of the tablet or capsule; 2) identification of polymer types of plastic bottles, pieces of plastic, or carpets for recycling purposes; 3) identification of gypsum plaster board material to determine whether the plaster board is from the source stated on the packaging or printed on the plasterboard or whether it is counterfeit; 4) identification of materials such as plastics, carpet, wood, cloth, and paper for forensic purposes (such as to determine if a fiber sample from a crime scene matches a sample from a known source); 5) determination of the authenticity of liquor and wine products; and 6) detection of materials containing significant amount of asbestos. Examples of quantification of chemical components include, but are not limited to, determining the concentration of the active ingredient in a pharmaceutical tablet or capsule or the concentration of fat and protein in a food sample.

Described herein are both a device and a method for identifying solid and liquid materials using near-infrared transmission spectroscopy combined with multivariate calibration methods for analyzing the near-infrared spectra. One important application of the device and method of the disclosure is the detection of counterfeit drug tablets, capsules and also liquid medications. Near-infrared transmission spectroscopy is employed within either the 700-1100 nm or the 900-1700 nm wavelength range to identify solid or liquid materials and to determine whether they match a specific known material, chemical compound, or product. The theoretical basis for the ability of transmission or reflection spectroscopy in the near-infrared spectral range to identify materials comes from two factors contributing to the spectra: 1) vibrational overtone absorptions present in this wavelength range that are directly related to the molecular structure of the material; and 2) spectral features related to light scattering from the sample. The light scattering effects are related to the inhomogeneous properties of the material such as grain or particle size and particle shape and size distribution, which influence the shape of the spectral baseline. Light scattering can be important in liquids containing suspended solids. The disclosed device and method could also be used to determine the concentration of specific chemical components in a solid or liquid sample.

One embodiment uses an array, preferably circular ring shaped, of near-infrared light-emitting diode (LED) light sources, each emitting at a different center wavelength to minimize the number of LEDs involved, together with a miniature dispersive optical spectrometer module incorporating an array detector [herein referred to as an optical spectrometer module] to measure a near-infrared transmission spectrum through the entire thickness of the solid or liquid sample being analyzed. An optical efficiency enhancing element of an optical concentrator, optical waveguide, or lens is used to increase the efficiency of transmission of light from the LED array to the sample. Options for this optical efficiency enhancing element include, but are not limited to: 1) a cone or compound parabolic shaped concave reflector element, or compound parabolic lens element; or 2) a solid glass or hollow metal (or metal coated) waveguide element of polygonal or an elliptically distorted polygonal cross section, to enhance the LED illumination intensity at the sample and also provide illumination that is more spatially homogeneous with respect to the multiple LED wavelengths over the sample area being illuminated. The LED array can have two different configurations: 1) an array of individually packaged LEDs designed for emission at a narrow angle of 30 degrees or less, each with integral collimating lens, with the optical axis of each LED pointing towards the center of the sample and sample aperture which would be used together with the cone or compound parabolic concentrator element; or 2) a monolithic circular array of LED chips mounted on a substrate which is used together with the waveguide element.

A different embodiment involves coupling the LED illumination light from the LED array into a bifurcated fiber-optic reflection probe where one or more optical fibers relay LED illumination light from the LED source to the sample and a separate optical fiber receives diffusely reflected light from the sample and relays it to the input of the spectrometer module that is used as the detection system. Examples of analysis applications that use this bifurcated fiber-optic reflection probe together with the analyzer include, but are not limited to, identifying loose powder samples in plastic bags or in glass or plastic containers, identifying powdered material or chemical samples not held inside any type of container, and identifying polymer types in samples of opaque plastics or synthetic carpets for the purpose of facilitating recycling.

The disclosed method includes analysis of the spectral data that is collected from unknown samples using a qualitative multivariate calibration analysis method such as Partial Least Squares Discriminant analysis. The multivariate calibration analysis of the near-infrared spectral data is used to determine whether the spectrum of an unknown material sample matches that of a known standard material or whether the sample is significantly different than the known standard material (i.e. different could mean being counterfeit). The multivariate calibration algorithm applies a calibration model, based on a set of calibration spectra (of known samples), to the unknown sample spectrum to determine the degree of match between the unknown sample and known calibration samples used to measure the calibration spectra. Multivariate calibration algorithms that can be used for identifying materials from their near-infrared spectra include: Partial Least Squares Discriminant analysis; Principle Component Analysis Mahalanobis distance based discriminant analysis; Soft Independent Modeling of Class Analogy (SIMCA); K-nearest neighbor method, Support Vector Machine (SVM) analysis; Linear Discriminant analysis; and Classical Least Squares Discriminant analysis. The result of the combination of the near-infrared analyzer with the multivariate calibration analysis is a device and method for reliably identifying solid materials that is lower cost and more portable than existing optical spectroscopic devices and methods. The optical analyzer may also employ multivariate calibration analysis methods such as Partial Least Squares that are designed to quantify particular chemical components in a sample so that the optical analyzer can be used in a quantification mode.

FEATURES AND ADVANTAGES

The disclosed system and method has significant advantages over existing portable spectroscopic analyzers known for use with drug or other material identification, including lower manufacturing cost, smaller size, lower power consumption during operation, shorter data collection time, the ability to measure all the way through drug tablets or capsules, avoidance of any eye hazards that exist with laser-Raman based analyzers, and a more mechanically robust and longer lived light source.

BRIEF DESCRIPTION OF THE DRAWINGS

In the drawings, closely related figures and items have the same number but different alphabetic suffixes. Processes, states, statuses, and databases are named for their respective functions.

FIGS. 9 A, B, & C are diagrams of a sample holder insert for liquid samples with built-in diffuser/beam homogenizer to increase the angular uniformity and the wavelength spatial uniformity of the LED light entering the liquid sample in a cuvette. This sample holder insert is compatible with the analyzer system where the liquid sample holder insert would be used in place of the tablet/capsule holder insert. This liquid sample holder insert fits into the same mounting bracket that holds the tablet/capsule sample holder insert.

FIG. 10 is a detailed diagram of an embodiment of near-infrared analyzer system showing use of a compound parabolic reflector as the concentrator element.

DETAILED DESCRIPTION, INCLUDING THE PREFERRED EMBODIMENT

Operation

In the following detailed description, reference is made to the accompanying drawings which form a part hereof, and in which are shown, by way of illustration, specific embodiments which may be practiced. It is to be understood that other embodiments may be used, and structural changes may be made without departing from the scope of the present disclosure.

Figure 1:
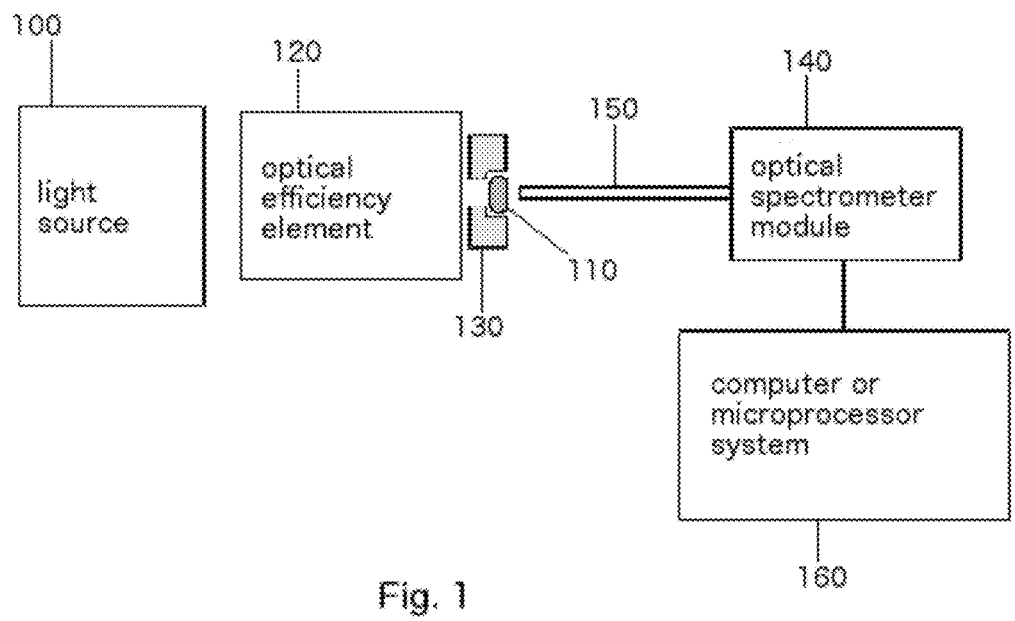
FIG. 1 is a general block diagram of near-infrared analyzer for identification of materials.

Referring to FIG. 1, a first basic part is light source 100, preferably a circular ring shaped, LED array with the optical axis of each LED pointing towards the center of a sample aperture, where the light source either covers the 700-1100 nm or the 900-1700 nm wavelength range. The wavelength range of 700-1100 nm corresponds to Si based array detectors (Si photodiode, Si-CCD. Si-CID, Si-CMOS) and covers the second and third vibrational overtone region of the near-infrared spectral range. The wavelength range of 900-1700 nm corresponds to InGaAs based array detectors and covers the first and second vibrational overtone region of the near-infrared spectral range. The light source may be continuously powered with batteries or a DC power supply and the light source may be either a LED array or a tungsten halogen lamp. In the case of the LED array light source, all the LEDs are on simultaneously and operating in a continuous emission mode. A tungsten halogen lamp light source is similarly operated in continuous mode. Following an optical path from light source 100 to sample 110 to detection system, the next component is the optical efficiency enhancing element 120, such as an optical concentrator or optical coupling element, which is followed by the sample that is being analyzed. The sample can be either solid, powder, or liquid. In the preferred embodiment the sample is positioned within sample holder system 130.

Figure 2A:
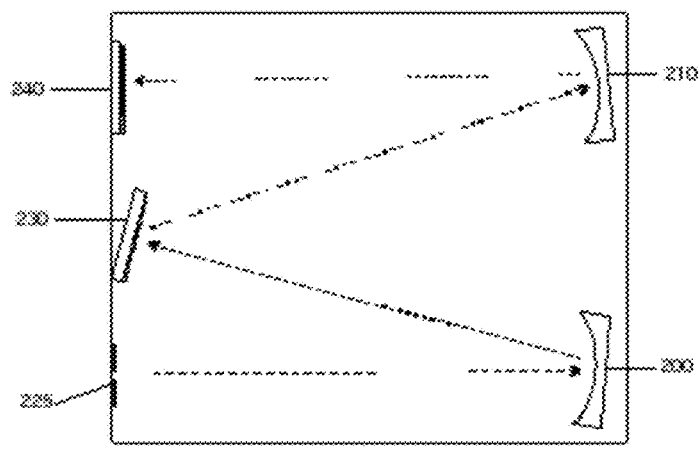
FIGS. 2 A, B, & C are various optical spectrometer configurations.
Figure 2B:
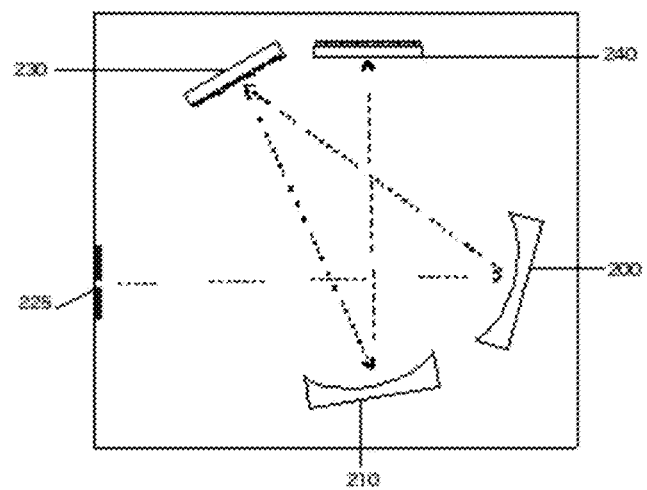
Figure 2C:
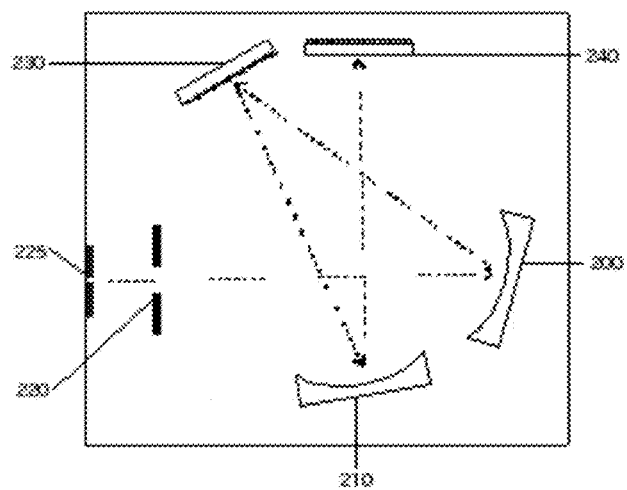
Figure 26:
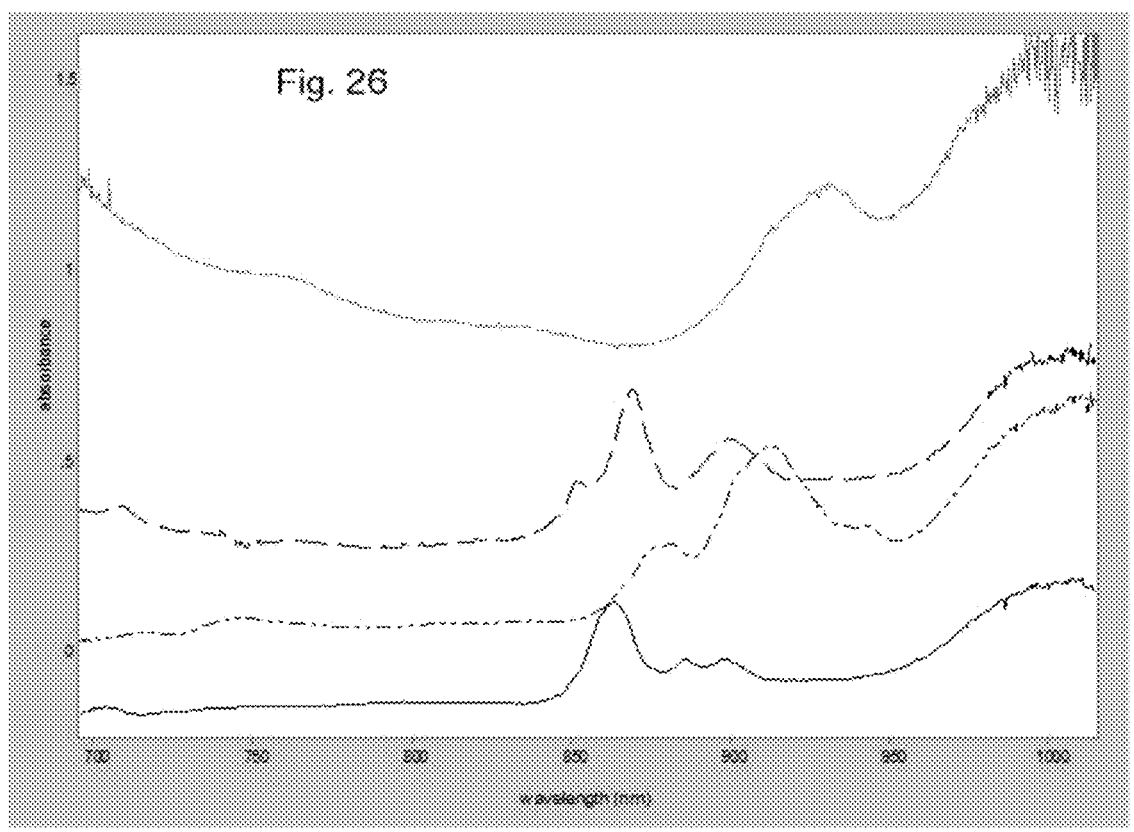
FIG. 26 shows measured spectra of drug tablets, with the upper curve (solid line) showing vitamin D, the upper middle curve (dashed line) showing Tylenol, the lower middle curve (dashed and dotted line) showing Motrin ibuprofen, and the bottom curve (solid line) showing Bayer aspirin.

The sample is followed by optical spectrometer module 140 with a slit at its input followed by collimating optics, followed by a dispersive element such as a diffraction grating or a prism (or combination of multiple prisms). In the case of a diffraction grating as the dispersive element, the diffraction grating can be either of the reflection or transmission type, and of planar geometry. The optical spectrometer module may have an optional fiber-optic element 150 to relay the transmitted light from the sample (or reflected from the sample) to the input slit of the optical spectrometer module. If a fiber-optical element is not used it is preferable to have a glass, fused silica or sapphire window in front of the spectrometer input slit to prevent foreign matter from entering the spectrometer slit. The dispersive element in the optical spectrometer module is followed by focusing optics and then a linear array detector. The collimating and focusing optics that are present before and after the dispersive element can either be concave mirrors, lenses, or a combination of both. Referring also to FIGS. 2 A, B, & C, in a preferred spectrometer design which incorporates a reflective diffraction grating dispersive element, the spectrometer design is a standard Czerny Turner (FIG. 26A) or crossed Czerny Turner configuration (FIGS. 26 B & C). Additional optical elements in the spectrometer such as flat mirrors may also be used in conjunction with collimating mirror 200 and focusing mirror 210 to provide additional folds in the optical paths. As shown in FIG. 2C, an optional input aperture 220 may be used to reduce stray light in the spectrometer, where the aperture is located between spectrometer input slit 225 and the first beam collimating optical element or between the input slit and spectrometer diffraction grating 230 in the case of a concave reflective grating. The linear detector array 240 is followed by an image readout circuit which may include an integration circuit, a multichannel analog/digital conversion circuit, and finally a memory buffer circuit that is interfaced with computer or microprocessor system 160. The memory buffer circuit function may be incorporated into the computer or microprocessor system as a memory module for storage, such as a hard drive. An alternative optical spectrometer module configuration employs a concave reflective diffraction grating as the dispersive element and does not use the separate collimating and focusing optics because the concave mirror aspect of the concave grating serves the function of the collimating and focusing optics.

The linear detector array of the optical spectrometer module can be a silicon charged-coupled device (Si-CCD) array or a silicon metal oxide semiconductor (Si-CMOS) array, or a silicon (Si) photodiode array or a Si-CID (charge injection device) array, when the multi-LED source covers the 700-1100 nm range. The linear detector array can alternatively be an Indium gallium arsenide (InGaAs) photodiode array that has a detection range of 900-1700 nm and is used together with an LED array light source emitting in the same wavelength range. The minimum spectral resolution that is desired for the 700-1100 nm spectral range is a resolution that corresponds to the sharpest spectral features that are typically present in condensed phase organic compounds which is about 10 nm (full width at half maximum of the spectral peak). To achieve a spectral resolution of 10 nm over the 700-1100 nm range one needs at least one wavelength point every 5 nm, which corresponds to 80 wavelength points. Commercial detector arrays are normally only available with the number of detector elements or pixels equal to a power of 2. A detector array with 128 elements would be the minimum power of 2 that could achieve a spectral resolution of 10 nm over the 700-1100 nm range. For the 900-1700 nm range the minimum spectral resolution needed is also about 10 nm, requiring 160 wavelength points for this 800 nm range and an InGaAs detector array with at least 256 pixels. The spectrometer module may also include gated integrator electronics for each detector array element and analog/digital convertor circuits to read the data from the detector array and integrators into a memory buffer for collection and temporary storage. The spectrometer module has an associated computer or microprocessor system for processing, display and analysis of the spectra data. The computer or microprocessor interfaced to the spectrometer controls the spectral data collection functions of the spectrometer, and may contain the memory buffer or input values from the memory buffer. The computer/microprocessor system may be a dedicated controller or any type of computing device, including but not limited to mobile computers such as a smart cell phone or a notebook computer. The computer/microprocessor system may have wired or wireless connection to a network, such as the internet, to transmit results or collected data to a central server or for off-site processing and analysis. Location data, such as that provided by a global positioning system (GPS) which may be connected to or part of the computer/microprocessor system, may be attached to the results or collected data for recording or transmittal. The spectrometer spectral acquisition software includes the ability to average multiple spectral scans and to select the integration time of the integrators associated with the linear detector array. In most embodiments, the optical analyzer system, including the multi-LED light source and the spectrometer module, are used to measure transmission spectra through solid or liquid samples and to analyze the spectra to provide identification of the solids or liquids being measured. Reflection spectra can also be measured using a fiber-optic reflection probe coupled to the spectrometer module and LED array light source.

Optical spectral data that is used for qualitative (identification) or quantitative analysis is normally processed into absorbance vs. wavelength units for transmission spectra or $-\log_{10}$(reflectance) units for reflectance spectra. The absorbance and log(reflectance) spectra require a dark spectrum and a light source reference spectrum to be collected first to produce the final spectra used for analysis. A dark spectrum is an intensity vs. wavelength spectrum that is taken with the spectrometer light source blocked or turned off, and the light source reference spectrum for the absorbance case is a spectrum taken without any sample present in the sample holder, or with a special reference sample in the sample holder. In the case of a log(reflectance) spectrum, the light source reference spectrum is a reflectance spectrum taken of a reflectance standard sample of known reflectance. The definition of absorbance and $-\log$(reflectance) follows:

$$\text{Absorbance}(\lambda) = -\log_{10}[(\text{sample transmitted intensity}(\lambda) - \text{dark}(\lambda))/(\text{reference intensity}(\lambda) - \text{dark}(\lambda))]$$

$$-\text{Log(reflectance)}(\lambda) = -\log_{10}[(\text{sample reflectance}(\lambda) - \text{dark}(\lambda))/(\text{reference stand·reflectance}(\lambda) - \text{dark}(\lambda))]$$

where $\lambda$ is the wavelength of the light.

For the purpose of identification of drug authenticity or material identification, the near-infrared absorbance spectral data of samples measured with the optical analyzer system is analyzed using software implementing standard multivariate calibration classification algorithms. These standard algorithms include: Partial Least Squares discriminant analysis, Principle Component Mahalanobis Distance discriminant Analysis, Soft Independent Modeling of Class Analogy (SIMCA), K-nearest neighbor method, Support Vector Machine (SVM) analysis, Linear Discriminant analysis; and Classical Least Squares Discriminant analysis. These are all standard classification algorithms commonly used in NIR spectral analysis which can use all the data points in the spectrum. The analysis algorithm, which is implemented on the computer, acts as a spectral pattern recognition routine and has both a calibration and prediction mode. A calibration training set of spectra measured for multiple authentic samples of a single drug or known material type are measured and then used to create a single drug or material multivariate calibration model with related collection settings. Typically, the calibration spectra are measured for 10 to 50 samples from different drug or material lots of each drug or material. A different model is created and retained by the system for each material or drug type. In the prediction mode, the calibration model algorithm, which is saved on the system computer, is applied to an unknown spectrum (spectrum of unknown sample) to generate a match score which is used to determine the unknown drug or material sample authenticity, based on the magnitude of the match score. Tests with known validation samples can be used to set a match score threshold value to distinguish authentic from counterfeit or significantly different drugs or materials. Alternatively, a multivariate calibration model can be created for multiple drug types or material types where the training set includes multiple samples of each of the different drug or material types that need to be tested for. Materials other than drugs that this multivariate spectral analysis approach can be used for include: plastics, chemicals, minerals, forensic paper, plastic, cloth, fiber, or wood samples, and alcoholic beverages.

In addition to drug and material identification, the near-infrared spectral data from samples measured with the optical analyzer system can also be analyzed for quantification purposes where the goal is to determine the concentration of specific chemical species or materials, or to determine some other quantitative value of a material such as the octane rating of gasoline. For analysis of the spectral data for quantitative purposes, standard multivariate calibration quantification algorithms are used such as: Partial Least Squares, Principle Component Regression, and Classical Least Squares.

One important application is the identification of counterfeit drugs, including drug tablets, capsules, and liquid medications. In addition, alternative embodiments of the analyzer system can be used to measure diffuse reflectance spectra and provide identification for powdered or solid samples. Samples that are preferably measured using diffuse reflectance sampling include powdered ingredients used to manufacture drug tablets of capsules, illegal drugs in plastic bags, mineral or rock samples, and opaque polymer samples such as recycled plastic pieces and synthetic carpets. In addition to authentication of drugs, the optical analyzer may also be used for quantification of particular components of drugs such as the active ingredient. Such quantification is important both for characterization of the active ingredient concentration in potentially counterfeit drugs and also for analysis of drugs that may be at risk from exposure to adverse environmental conditions such as high temperatures or humidity which could reduce the concentration of the active ingredient.

Figure 3:
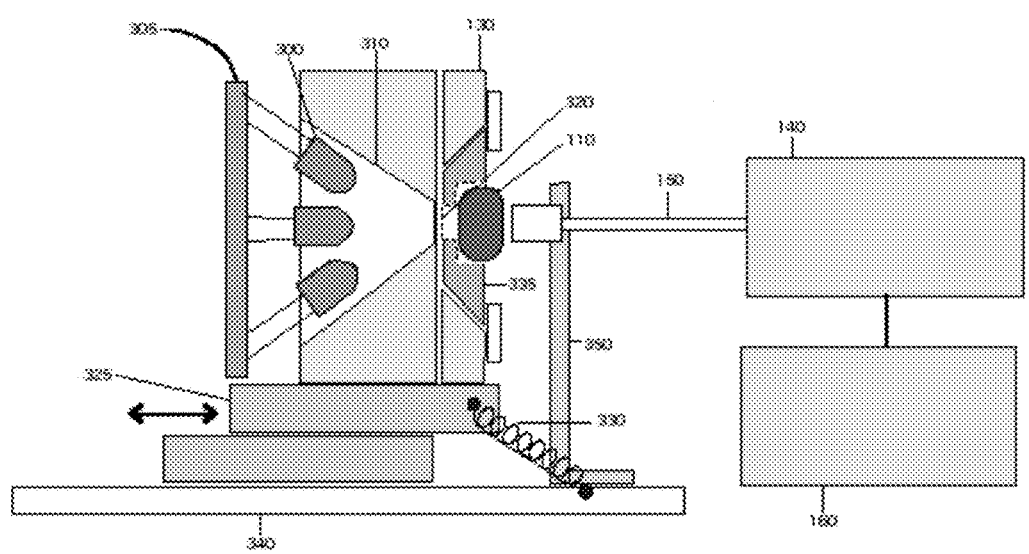
FIG. 3 is diagram of a preferred embodiment of the near-infrared analyzer for identification of materials.

FIG. 3 shows a diagram of one embodiment of the optical analyzer system where light source 100 is ring shaped multi-LED array 300 of individually packaged LEDs, each emitting at a different near-infrared wavelength band, which have a molded-in lens at the emitting end of the LED package, the LED array powered by power supply 305. An alternative light source may be a tungsten-halogen lamp. An individually packaged LED is a LED encapsulated in plastic or packaged in a metal can with plastic encapsulation. Use of the ring-shaped geometry, and emission on different wavelengths for each LED, is done to minimize the number of LEDs needed and therefore reduce cost of construction, but differently shaped arrays may be used. The number of LEDs needed varies with spectral range and LED intensity, with minimum LED configurations using between four and twenty LEDs. The light source is followed by optical efficiency enhancing element 120. In an embodiment with an LED array, the optical efficiency enhancing element is preferably optical concentrator 310. The optical efficiency enhancing element increases efficiency of light transmission from the light source to sample holder 130 which is shown holding a tablet or capsule sample 110. With an LED light source, the LEDs preferably each have their optical axis pointing towards the center of the sample aperture 320 and sample 110. Directing the optical axes towards the sample helps concentrate the light on the sample. The sample is followed by optical fiber element 150 which couples to an input slit of dispersive spectrometer module 140 that is used as a detection system. The spectrometer module interfaces with computer or microprocessor system 160 to control the spectrometer spectral data acquisition functions and also to perform spectral data processing, display and analysis functions. Optional translation stage 325 may be used to mount the light source, associated efficiency enhancing element, and sample holder system. The translation stage allows the light source and sample holder components to be translated away from the receiving fiber connected to the spectrometer module for the purpose of loading the sample into the sample holder and for removing the sample from the sample holder. The translation stage is preferably spring loaded, such as with spring 330, to maintain a small amount of pressure of the sample against the light receiving tip of the optical fiber that connects to the spectrometer module input or against the end of the fiber-optic connector that the tip is held in. The optical analyzer system shown in FIG. 1 is designed to measure transmission spectra of solid or powdered samples, including samples such as drug tablets and capsules that can have very high values of optical attenuation on the order of $10^4$. As will be discussed later, the sample holder can be easily replaced with a different sample holder that permits measurement of liquid samples that are contained in a cuvette.

To measure the light source reference spectrum, which is required to obtain absorbance spectra from the raw single-beam sample spectra, a special reference sample is used that is in the form of a disk or rectangular plate made from white Teflon or Spectralon (a form of compressed white Teflon powder). Teflon and Spectralon were chosen because they produce substantial light attenuation as a result of light scattering losses, but have no significant absorption bands in the 700-1700 nm range. Other materials that scatter light in the 700-1700 nm range and have no strong absorptions in this wavelength range, such as glass frit, could also be used for the reference disk or plate. The reference disk or plate is fabricated to have about the same diameter and approximately the amount of optical attenuation as the drug tablet or capsule samples or other solid samples that are being measured with the optical analyzer. The reference sample should have a similar absorbance value, meaning within a factor of 3 to 10, of the sample to be measured. For example, a Spectralon disk with a thickness of 4.4 mm and a diameter of 10 mm has an optical attenuation that is similar to that of many common drug tablets in that size range. For highly attenuating samples like drug tablets or capsules with attenuation on the order of $10^4$, it is not practical to directly measure a reference spectrum without an attenuating reference sample present, because the detection circuitry would be saturated by the combination of a high light level hitting the detector array and a high detection gain and/or integration setting that is required for such a sample. Lowering the integration time or signal gain of the detection system would be possible to compensate for the high light level without a reference sample present, but has disadvantages including increased complexity of the electronics and computer interface, and would require measuring separate dark spectra to be used for correction of the reference and sample spectra (instead of using the same dark spectrum for both). Spectralon or solid white Teflon would be used as a reference sample material for strongly attenuating sample materials, where the attenuation of the sample is a factor of 10 or more. For clear liquid or plastic samples, where the attenuation is less than a factor of 10, an attenuating reference sample material such as Spectralon or Teflon would not be used. The attenuation of the Spectralon or Teflon reference sample should be equal to or within a factor of 10 times higher than the attenuation of the sample being measured.

The optical concentrator element 310 may be a cone shaped reflector (with cone apex towards the sample aperture), a cone shaped lens, a compound parabolic reflector (with parabolic focus close to the sample aperture), a compound parabolic lens (with parabolic focus close to the sample aperture), or a compound elliptical reflector with one focus near the sample.

Figure 4:
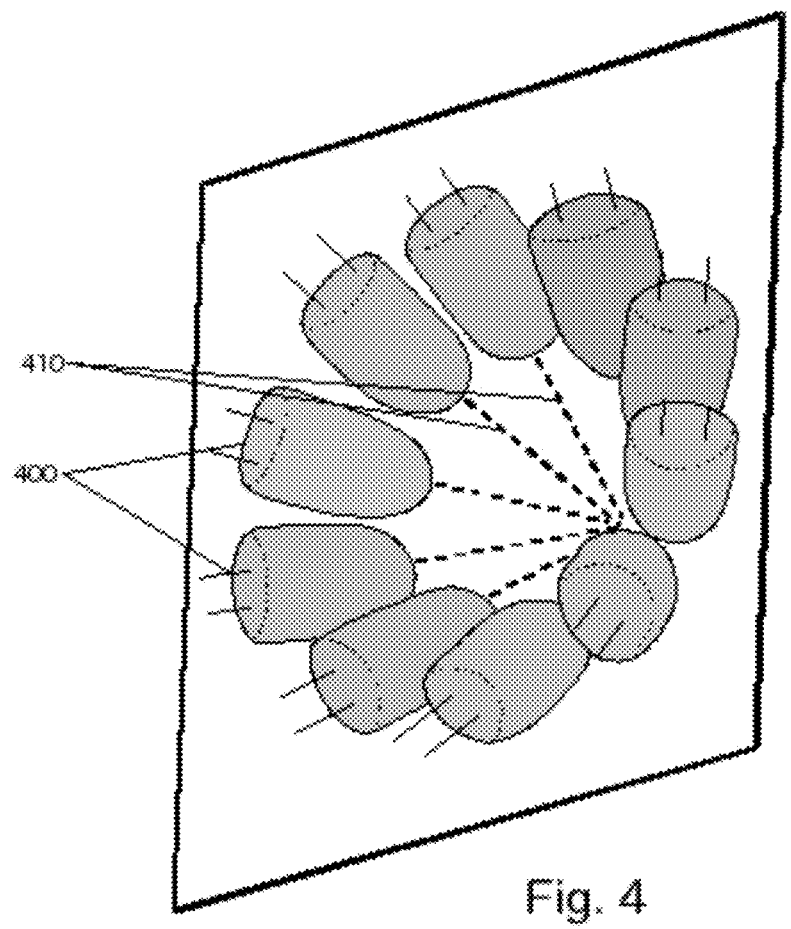
FIG. 4 is a three-dimensional rendering of circular ring-shaped multi-LED array of 10 LEDs, where the LED optical axes are mounted so that they all point to a common point with an angle of 45° with respect to the normal to the plane of the array. The LEDs in this LED array configuration are individually packaged with a clear polymer encapsulation with a molded-in lens.

FIG. 4 shows a diagram of one embodiment of the ring shaped multi-LED array 300 for individually packaged LEDs 400 which have molded-in lenses to help collimate the emitted LED light. The optical axis 410 of each LED in the ring shaped array is pointing towards the center of the sample aperture in the sample holder and the sample. In the embodiments employing the individually packaged LEDs, the LEDs may be mounted with their optical axis having an angle relative to the normal of plane of the array ring of between 55°-35°. A first order calculation of the optimal angle of a ring shaped array of LEDs can be made which is based on the spreading losses of the individual LED beams together with the losses associated with the LED beams hitting the sample at an angle. The spreading angle of the LED beams is about a 10° angle, where the intensity loss from this spreading is proportional to the square of the distance of the LED from the sample aperture. When the loss from the individual LED beam spreading is compared to the reduced illumination due to the LED beam hitting the sample at an angle, it was found that an LED array with the LED optical axes at a 45° angle to the normal to the LED array provides the optimal illumination intensity at the sample. However, second order factors such as the effects of the concentrator on the LED array angle vs. sample illumination intensity have not been taken into account and an error margin of ±10° is added to account for these second order effects.

Figure 5:
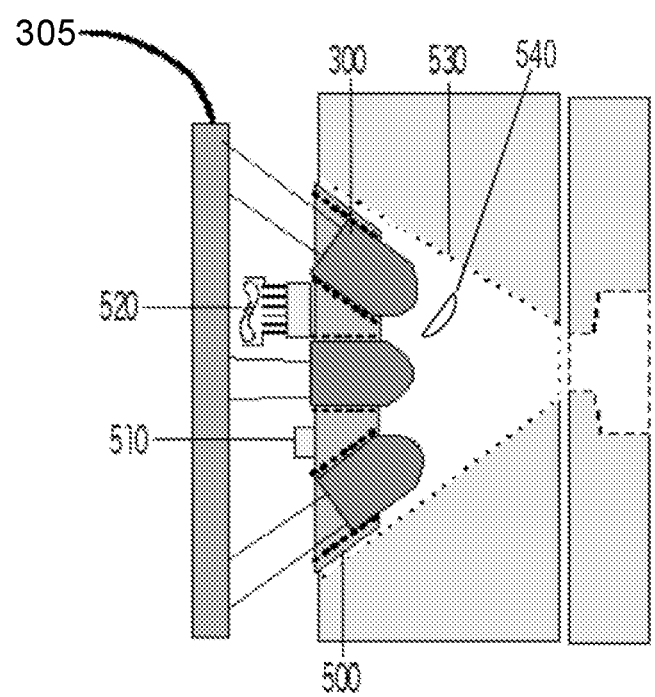
FIG. 5 is a diagram of a ring shaped LED array light source with LEDs mounted in a metal heat-sink plate which is thermostatically controlled using a thermoelectric cooler and a temperature sensor. The temperature sensor and thermoelectric cooler connect to a temperature control circuit. The thermoelectric cooler has heat dissipating fins and a miniature fan attached to its hot surface to help remove the heat extracted from the LED heat sink.

As depicted in FIG. 4, the LED optical axes have an angle of 45° with the normal to the plane of the LED ring. As shown in FIG. 5, in one embodiment the LEDs in array 300 may be mounted in a metal plate 500 that is thermostatically controlled using temperature sensor 510 and thermoelectric cooler element 520 mounted on the metal plate. The temperature sensor 510 and the thermoelectric cooler element 520 are connected to a temperature controller circuit that keeps the LEDs at a constant temperature. Another option is for some of the LEDs to be higher power LEDs individually packaged in a metal surface mount package with plastic encapsulation over the front side of the LED chip, where an external lens 540 may be used in addition to the molded-in LED lens to better collimate the LED light. The higher power LEDs are often designed with built-in or molded-in lenses that provide a very wide angle emission pattern. High power metal packaged LEDs are available that emit in the range of 40-90 mW of optical power while low power plastic encapsulated LEDs emit in the range of 3-18 mW of optical power. The higher power LEDs require mounting with heat sinking to a metal heat sink mount. The higher power LEDs have one portion of the metal package that must be in contact with the heat sink mount or plate, and as a result the mounting geometry may vary slightly from the arrangement shown in FIG. 3.

Current limiting resistors are wired in series with the LEDs and have resistance values chosen for each LED to provide the desired driving current for each LED that meets the minimum current limit for the LED and results in the desired emission intensity for that LED. The LED intensities may be adjusted to have the weaker long wavelength LEDs emitting at full power and the shorter wavelength LEDs emitting with reduced power to produce a balanced spectrum that is very similar in shape to that of a tungsten halogen lamp. FIG. 5 also shows one type of concentrator element 310, a cone shaped reflector 530, which helps concentrate LED light on the sample aperture and sample.

Figure 6:
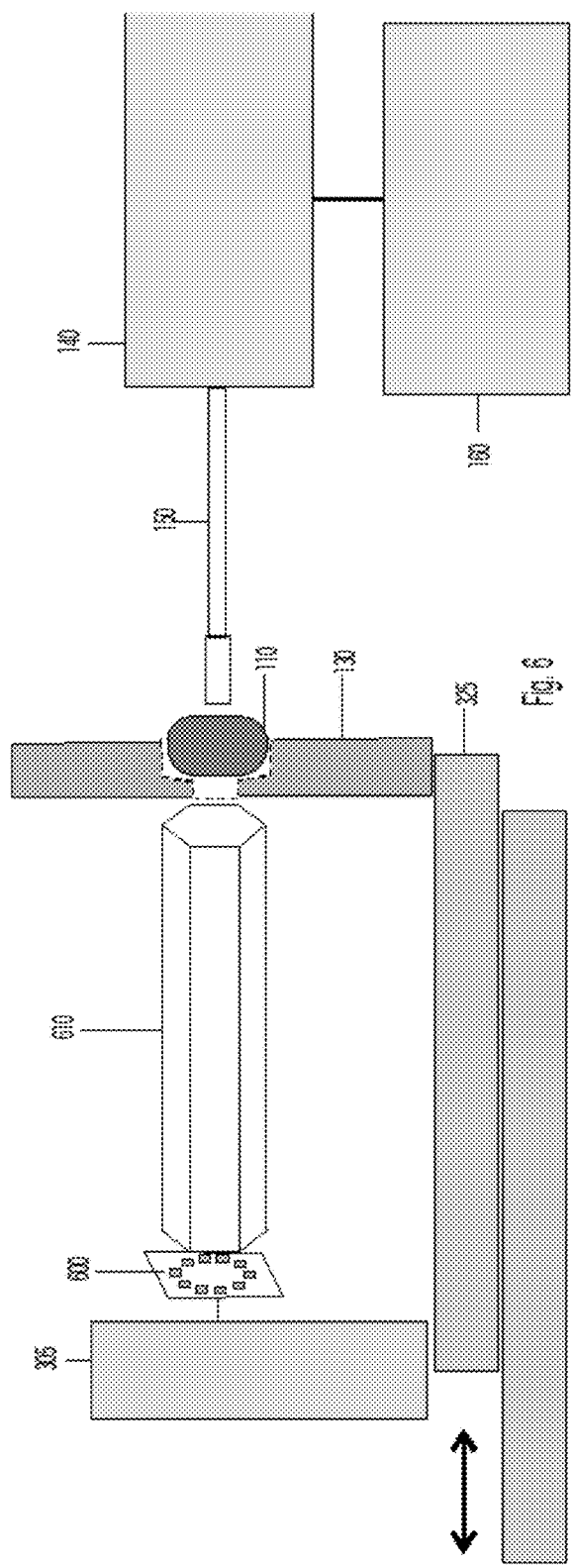
FIG. 6 is a general system diagram of near-infrared analyzer for identification of materials using a custom mounted monolithic array of LED chips (each emitting at a different center wavelength in the 650-1100 nm or 800-2500 nm wavelength range) mounted in a single package without any lenses. A solid glass or fused silica polygonal waveguide element is used to efficiently relay the light from the LED array to the sample and also to spatially homogenize the sample illumination light with respect to wavelength distribution.
Figure 7:
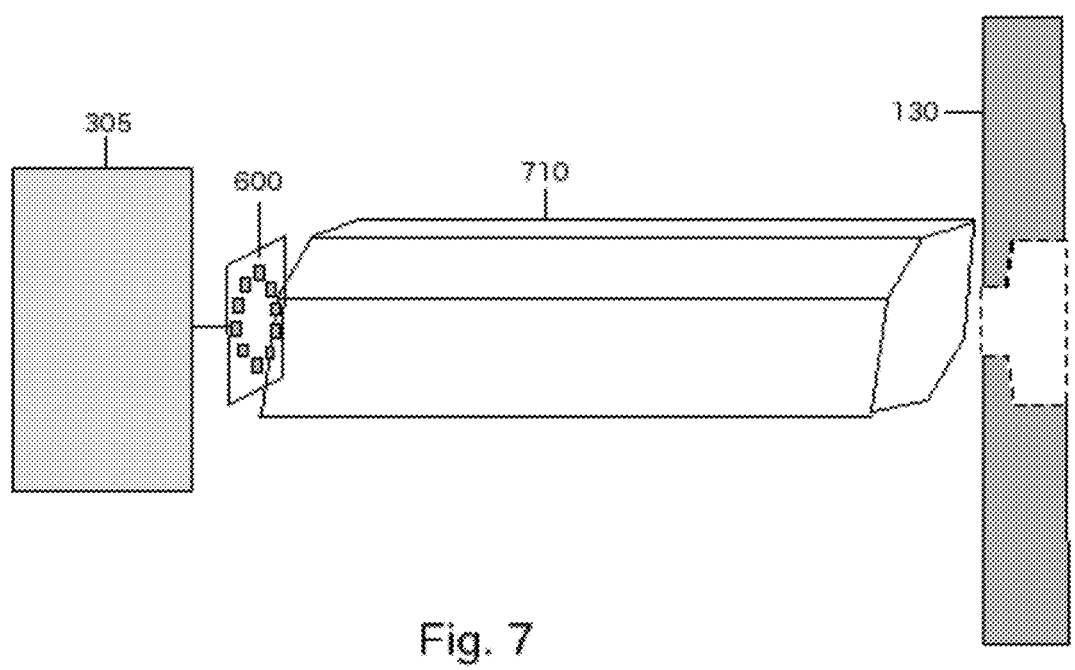
FIG. 7 is a diagram showing faceted elliptical polygon cross-section waveguide element used to relay light from monolithic LED chip array to sample. This waveguide has a cross-section that is an elliptical distortion of the waveguide element shown in FIG. 6.

FIG. 6 shows an alternative embodiment of the circular LED array 300 and associated optics, wherein the LEDs are in the form of a monolithic array of LED chips mounted on a flat substrate 600. The substrate surface surrounding the LED chips may be made of a material with high reflectivity in the short wavelength near-infrared range such as aluminum or a white ceramic material. The light output of the LED array may couple into a polygonal waveguide element 610 that efficiently relays the light to the sample aperture and the sample. FIG. 7 shows a variation of the polygonal waveguide element having an elliptical distortion. The waveguide shape shown in FIGS. 6 and 7 is a hexagon 610 and elliptically distorted hexagon 710, respectively. The waveguide shape as shown in FIG. 7 is also referred to as a faceted elliptical waveguide. Other types of polygon cross sections such as a pentagon or octagon could also be used. The use of a polygonal cross-section solid waveguide instead of a pure circular or elliptical cross-section waveguide achieves more homogenous mixing of the different wavelength band emissions of the LEDs. In both designs shown in FIGS. 6 and 7, the space between the LEDs and entrance surface of the waveguide element may optionally be filled with an optical encapsulant layer of clear optical epoxy or clear silicone sealant to protect the LED chips and also to lower the optical losses for the LED light entering the waveguide element. When a waveguide homogenizer element is used together with a monolithic LED chip array, a concentrator element is not needed. The monolithic LED chip array light source may also be modified to include a thermoelectric cooler with associated electric fan, a temperature sensor, and a temperature control circuit to maintain the monolithic LED array at a constant temperature.

FIG. 3 shows the preferred embodiment. This embodiment uses LEDs that are individually packaged with a molded-in lens and the optical concentrator element is a cone shaped reflective concentrator. The reflective cone concentrator helps to increase the LED illumination intensity at the sample. The receiving fiber of the diffraction grating spectrometer has its receiving end held in a mounting plate by means of a two part fiber-optic connect with an outer connector part and an inner connector part. This design has a sample holder system in which a tablet, or capsule, or rectangular cuvette holding a liquid sample, is first loaded into a removable sample holder insert 335. The sample holder insert is then inserted into a sample holder mount in the analyzer system, which requires pulling back the three part assembly of the multi-LED source plus the cone concentrator plus the sample holder mount which are all mounted on the upper section of a translation stage 325. After the sample holder insert is in place in the sample holder mount, the LED source/concentrator/sample holder assembly that is mounted on the translation stage upper section is slowly released so that the sample pushes against the end of the receiving optical fiber, or against the surface of the inner part of the fiber-optic connector of the receiving fiber of the diffraction grating spectrometer. Pressure to hold the sample against the receiving fiber inner connector surface is provided by springs 330 mounted between the translation stage upper section and analyzer system base plate 340.

Figure 8:
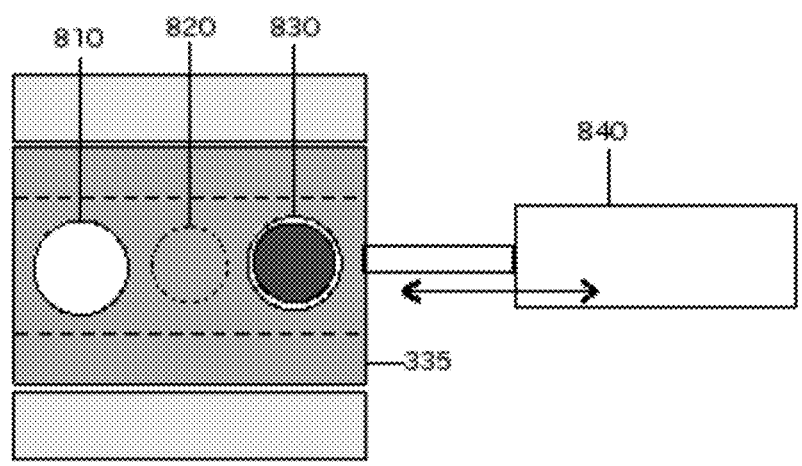
FIG. 8 is a detailed diagram of a preferred embodiment of a sample holder insert for holding tablet or capsule samples.

FIG. 8 shows more detail of the design of the sample holder insert 335 for drug tablets and capsules. A preferred sample holder insert for tablets and capsules has three measurement positions. One position 810 is for the sample to be measured, a second position 820 for blocking light transmission and allowing dark spectrum measurement, and a third position 830 for a reference sample such as a Spectralon or Teflon disk. Sample holders with different positions may also be used, such as a 2-position holder with positions for sample and reference, or single position in which sample or reference may be inserted. Placement of the sample holder at the different measurement positions may be automated by having the sample insert position being driven by a solenoid or linear motor actuator device 840 that is controlled by the computer/microprocessor system such that only one of the positions of the sample holder insert lines up with the sample aperture during a spectral measurement. Sample holders with different sized cavities may be used to hold drug tablets and capsules or other material samples of different size ranges. FIGS. 9 A, B, & C show top, side, and front views of a sample holder insert that is used for liquid samples which holds a cuvette 900 in which the liquid sample is contained. The cuvette is preferably made of borosilicate glass, fused silica, or clear polymer materials including acrylic and polystyrene polymers. The plastic cuvettes are very low-cost and considered disposable, but cannot be used with organic solvents or other liquids that dissolve or cause swelling in the polymer material. Borosilicate glass cuvettes are chemically resistant to almost all liquids and transmit well throughout the near-infrared spectral range. The plastic cuvettes have significant near-infrared absorptions for near-infrared wavelengths longer than 1100 nm. The liquid sample holder insert includes a white Teflon, Spectralon, or ground glass diffuser element 910 that is used to help redistribute the light emitted from the LEDs in the array so that the exiting LED light is more uniform with respect to wavelength as a function of angle. For an LED array with a large angle of the LED optical axes to the plane normal of the array ring, such as a 45° angle, the diffuser directs more light from the LED array through the sample cuvette and to the receiving spectrometer fiber than is possible without the diffuser. Without the diffuser, most of the light emitted by the 45° angle LED array misses the receiving fiber. A Teflon diffuser of only 0.03"-0.04" thickness is very effective for this purpose. The diffuser thickness needs to be sufficient to homogenize the angular distribution of the LED light that exits the sample aperture in the sample holder mount. If the diffuser is thicker than the minimum needed for this angular homogenization, then it will result in decreased light throughput to the sample and the spectrometer, and result in reduced signal/noise in the sample spectra. To measure the light source reference spectrum for liquid samples, a spectrum may be collected with the Teflon diffuser in place and either an empty cuvette, or a cuvette filled with a reference liquid (such as pure water for a water based sample) in the sample holder. For highly scattering liquids such as medications based on a solid powder suspension in water, an additional Teflon diffuser may be inserted in the sample holder insert for measurement of the reference spectrum, where the Teflon diffuser would provide similar attenuation to that of the liquid suspension sample.

The analyzer diagram in FIG. 10 shows a compound parabolic reflector 1000 as an alternative efficiency enhancing element 120 to the cone reflector shown in FIGS. 3 and 5. Compound parabolic reflectors are designed to provide significant concentration of light entering the large end of the concentrator at a wide range of angles. A compound elliptical mirror concentrator may also be used.

Figure 11:
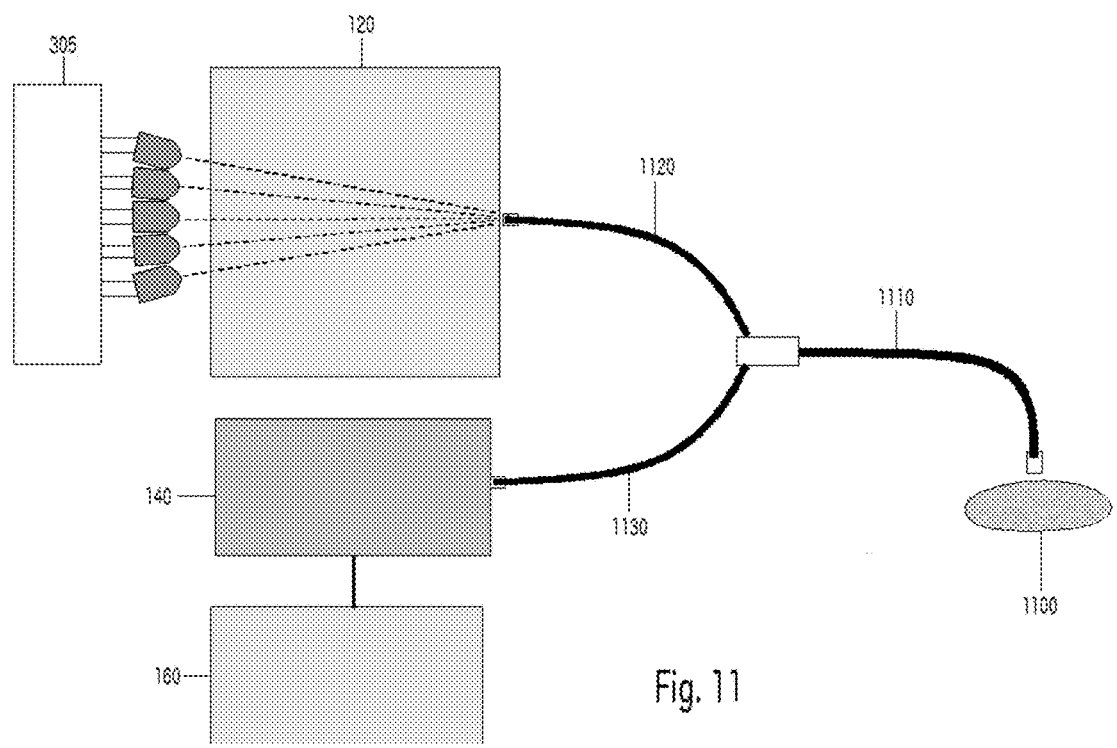
FIG. 11 is a diagram of a configuration of the analyzer system for measuring powder samples held in containers such as glass or plastic vials or bottles and also plastic bags by reflection sampling with a fiber-optic reflection probe. The optical concentrator element can either be a cone shaped reflector or a solid cone shaped refractive element, a compound parabolic reflector or a refractive lens, or a compound elliptical reflector or refractive lens, all with the small diameter end of the concentrator towards the illumination fiber tip. The optional optical homogenizer element can be a Teflon diffuser plate or a polygonal solid or hollow waveguide or a distorted elliptical cross section solid or hollow polygonal waveguide.
Figure 12:
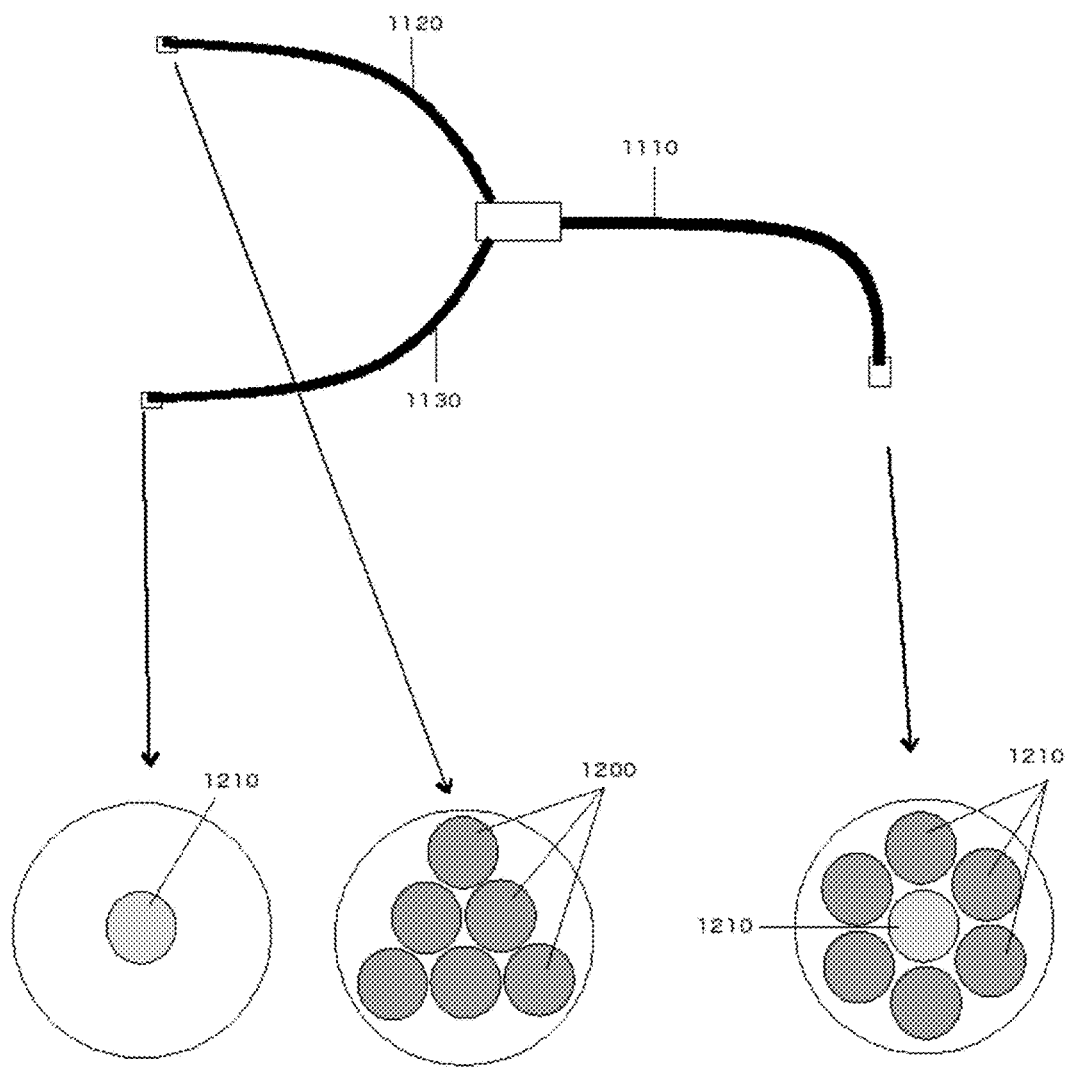
FIG. 12 is a diagram showing the detailed design of one possible configuration of the bifurcated fiber-optic reflection probe shown in FIG. 11. The fiber core diameters would all be about in the range of 0.4-1.0 mm.

The diagrams in FIGS. 11-12 show designs with a fiber-optic reflection probe and how the optical analyzer system is configured to measure diffuse reflection spectra using this fiber-optic probe. Measuring diffuse reflection spectra with a fiber-optic reflection probe is a commonly used sampling method for measuring NIR spectra of solid powder samples, and can also be used for mineral or rock samples, opaque polymer samples, and carpet samples. Powdered material samples can be measured by inserting the tip of the reflection probe directly into powder in a container or into a deposit of powder on a surface. Powder samples can also be noninvasively measured with the reflection probe tip held close to the surface of the powder or solid being measured. In addition, the reflection probe can be used to characterize powders contained inside of transparent glass or plastic bottles or vials, or inside of plastic bags 1100, where the tip of the reflection probe is located just outside of the container holding the powder. For these powder samples held in clear containers, the reflection probe measures through the wall of the container.

FIG. 11 shows a diagram of the optical analyzer system configured to measure diffuse reflectance spectra with a bifurcated fiber-optic sampling probe 1110. After passing through the optical efficiency enhancing element 120 the LED light is received by the illumination fiber-optic bundle 1120 which relays the LED light to the sample 1100. An optional optical homogenizer element may be included between the efficiency enhancing element and the illumination fiber-optic bundle. The homogenizer element may be either a simple disk or plate of white Teflon (with a thickness in the range of 0.5-2 mm) or a solid polygonal waveguide such as waveguide element 610. The homogenizer element helps improve the uniformity of the LED light reaching the sample with respect to spatial wavelength distribution over the sample area. The LED light reflected by the sample is collected into the receiving fiber that relays the reflected light to the spectrometer module input. To obtain optimal coupling of the light from the circular LED array into the illumination fiber bundle, an LED array with an angle of the LED optical axes relative to the array normal, in the range of 20-30° is preferable because of acceptance angles of typical optical fibers. An LED array angle of about 45° is more optimal for measuring solid samples by transmission sampling, but still can be used to measure reflectance spectra with the configuration shown in FIG. 11. FIG. 12 shows the detailed design of one configuration of a bifurcated fiber-optic reflection probe. The probe design in FIG. 12 has an illumination fiber bundle 1120 consisting of 6 optical fibers 1200 having the same diameter as a central fiber 1210 used to receive the reflected light from the sample. A reflection fiber 1130 and the illumination fiber bundle are initially separated and then combined into one bundle in the middle of the fiber-optic probe. The central reflection receiving fiber 1210 has a core diameter close to 400 µm. In the design shown in FIG. 12 the illumination fibers are of the same diameter as the receiving fiber. In addition to the configurations of the optical analyzer for measurement of diffuse reflectance spectra using a multi-LED light source constructed with an array of individually packaged LEDs, as shown in FIG. 11, a multi-LED light source based on a ring shaped monolithic LED chip array may also be used. The monolithic LED chip array light source may be coupled to the illumination fiber bundle of the fiber-optic reflection probe using a polygonal or elliptically distorted polygonal waveguide element.

To measure a light source reference spectrum for the diffuse reflectance sampling mode, a flat Spectralon or Teflon disk may be used as a reference sample. This reference sample may be placed in the same position as the sample with respect to the reflectance probe tip for the reference spectrum measurement. Alternatively, an aluminum plate with a roughened surface may be used as a reference sample.

Figure 13:
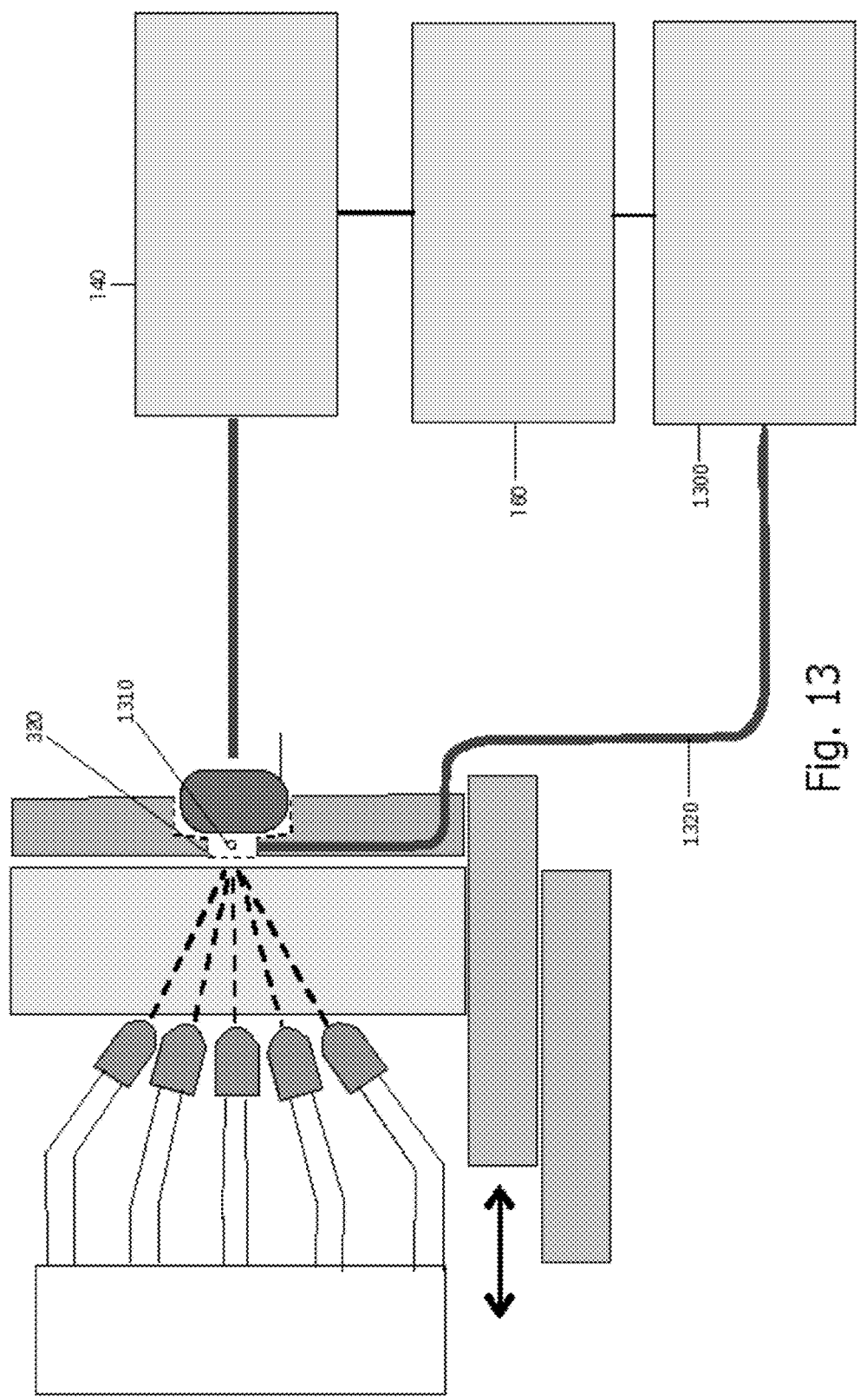
FIG. 13 is a diagram of an embodiment of the optical analyzer system that includes separate sample and light source reference optical spectrometer modules and an extra fiber-optic element to relay a small portion of the LED light that illuminates the sample to the reference spectrometer module. This configuration of the analyzer would allow a new light source reference spectrum to be measured simultaneously every time a sample spectrum is measured.

FIG. 13 shows an embodiment of the optical analyzer system that includes a second optical spectrometer module 1300 (dispersive prism or diffraction grating spectrometer module with array detector) to allow simultaneous measurement of a light source reference spectrum every time a sample spectrum is measured. The measurement of the reference spectrum for every sample measurement can improve the signal/noise in the final sample absorbance spectrum and also reduce distortion in the absorbance spectrum due to drift of the light source spectral shape and intensity. Without the extra reference spectrometer module, the reference spectrum is typically measured once every 20 or 30 minutes. Light from the LED array is reflected from a small aluminum or Teflon rod or wire 1310 located near the center of the sample aperture, and a portion of the reflected light enters a reference receiving optical fiber 1320 that sends light to the reference spectrometer module.

Figure 14:
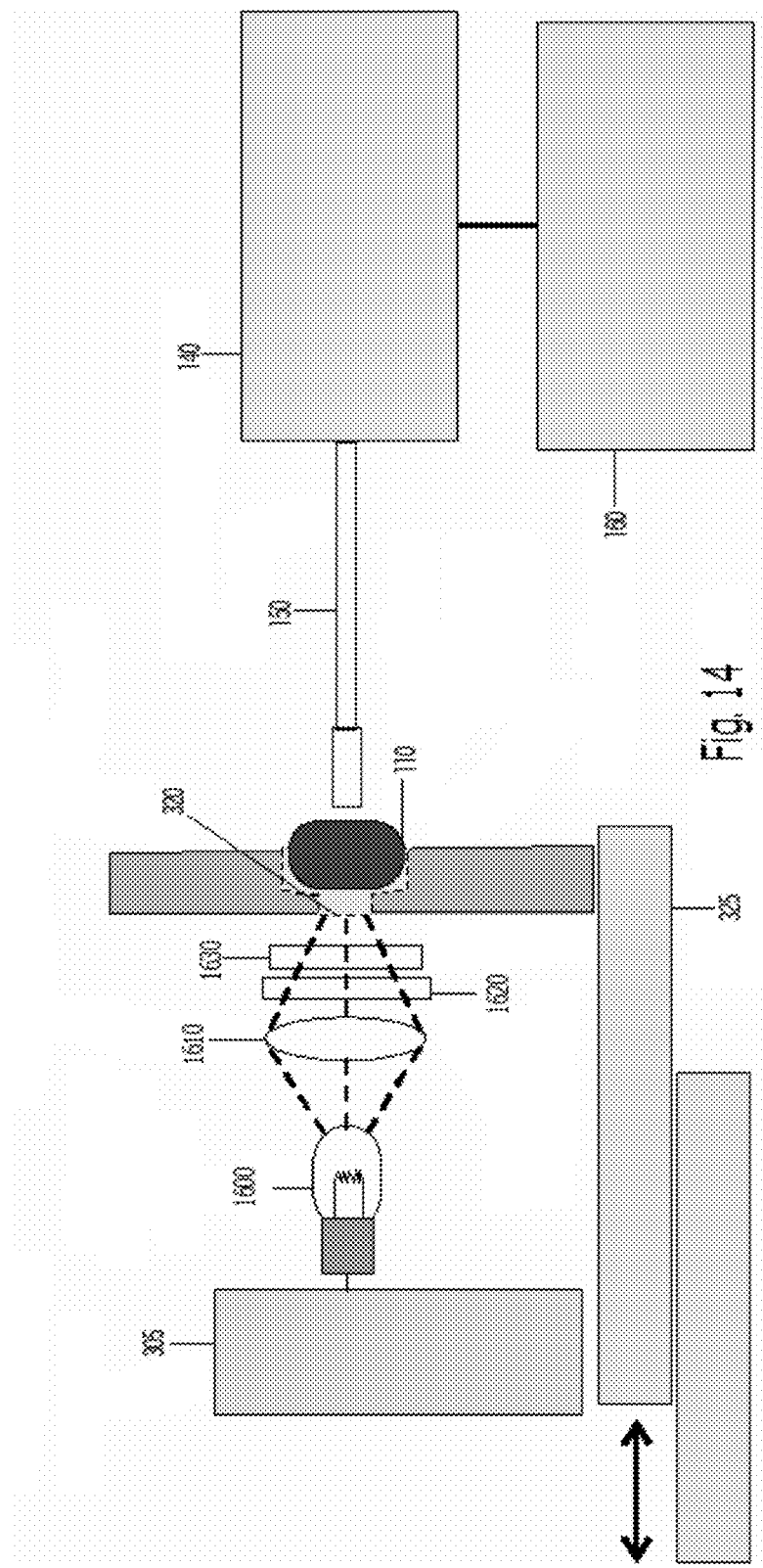
FIG. 14 is a diagram of near-infrared analyzer system (700-1100 nm or 900-1700 nm wavelength range) with a tungsten-halogen light source that uses a glass or fused silica lens to focus the illumination light on the sample aperture.
Figure 15:
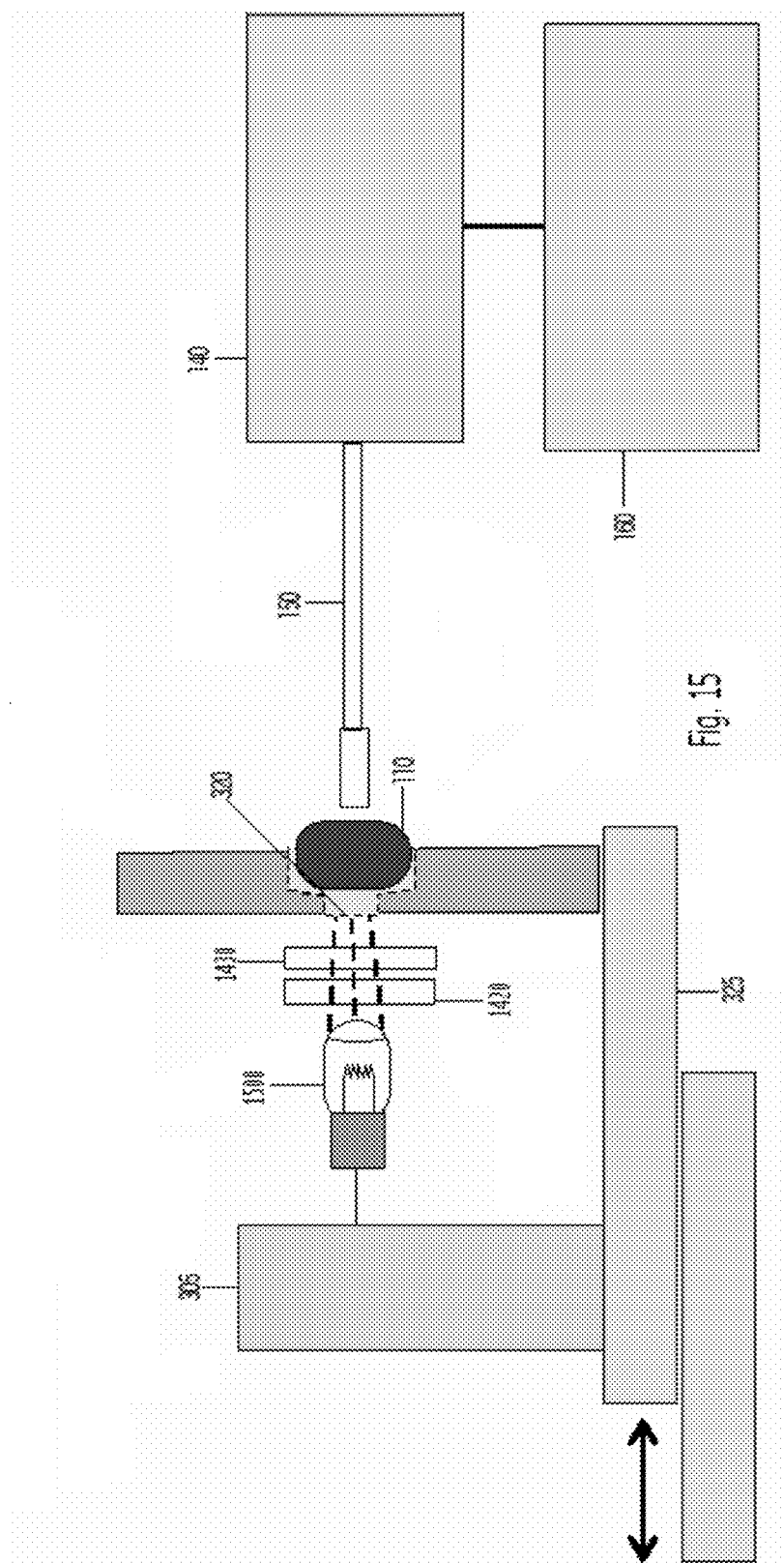
FIG. 15 is a diagram of near-infrared analyzer system (700-1100 nm or 900-1700 nm wavelength range) with a tungsten-halogen light source that uses a fused silica lens that is molded into the end of the lamp envelope to focus the illumination light on the sample aperture.
Figure 16:
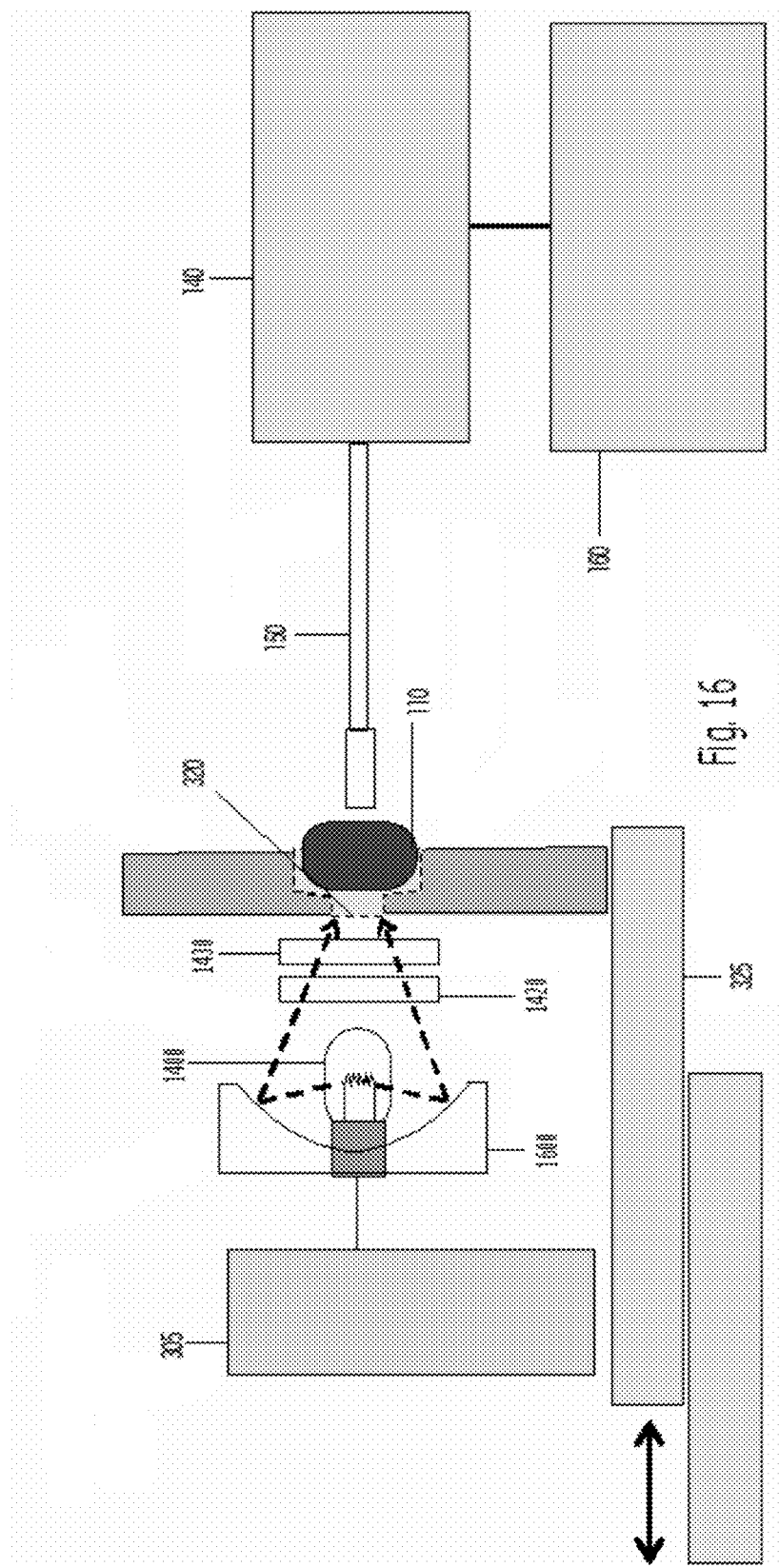
FIG. 16 is a diagram of near-infrared analyzer system (700-1100 nm or 900-1700 nm wavelength range) with a tungsten-halogen light source that uses a concave front surface aluminum mirror to focus the illumination light on the sample aperture.
Figure 17:
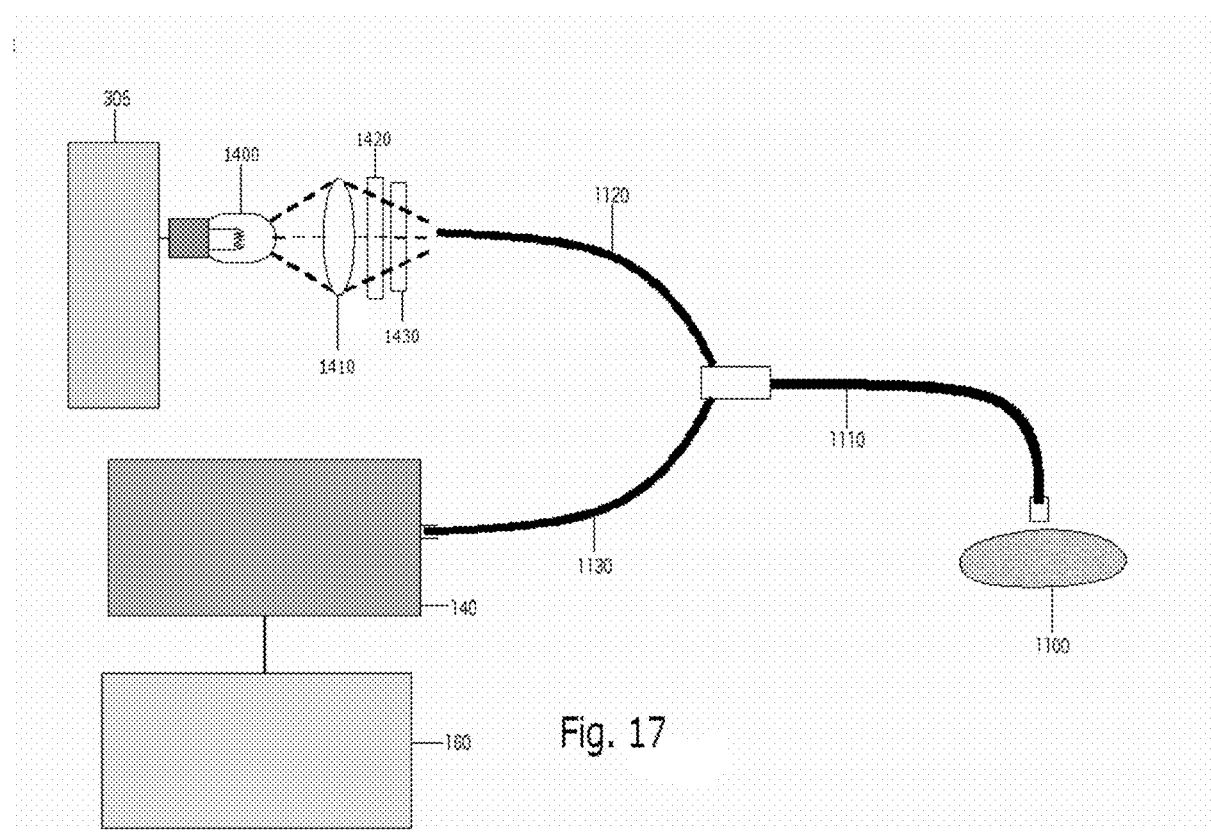
FIG. 17 is a diagram of near-infrared analyzer system (700-1100 nm or 900-1700 nm wavelength range) with a tungsten-halogen light source for diffuse reflectance sampling with a bifurcated fiber-optic reflectance probe.

An alternative embodiment replaces the LED array with a tungsten-halogen lamp light source. With such a light source, a focusing element is needed to focus the lamp emission onto the center of the sample aperture, and long pass and short pass optical filters to restrict illumination to the 700-1100 nm wavelength range. FIG. 14 shows an embodiment with a tungsten-halogen lamp 1400 where a glass or fused silica lens 1410 is used to focus or concentrate the illumination light on the sample aperture. Long pass optical filter 1420 and short pass optical filter 1430 are employed to restrict illumination to the appropriate range to avoid overheating the sample. The NIR diffraction grating spectrometer 140 has a Si array detector and the following properties: spectrometer internal collimating and focusing optics (concave mirrors or lenses) with a focal length of ≤40 mm, an enclosure with dimensions 7.5 cm×5 cm×2.5 cm, spectral resolution in the range of 0.5-10 nm, and with a spectral collection time that is 30 seconds. These limits for the spectrometer are only for the analyzer system with the tungsten-halogen light source. These spectrometer enclosure, and internal optics, limits correspond to a new class of highly miniaturized diffraction grating spectrometers with Si array detectors that have become available as commercial products since 2011, but have not previously been used for material identification. FIG. 15 shows a similar embodiment where the light source is a tungsten-halogen lamp with a built-in lens 1500 acting as the focusing element. FIG. 16 shows another alternative with concave front surface aluminum mirror 1600 acting as the focusing element for the tungsten halogen light source. Similar to FIG. 10, a modification of the embodiment with the tungsten halogen light source enables diffuse reflection sampling. Similar to FIG. 11, FIG. 17 uses a bifurcated fiber-optic probe 1110 and replaces the sample holder and aperture with an illumination fiber bundle 1120 that relays the light from the tungsten halogen light source 1400 to the sample, and a single element optical fiber 1130 that couples to the spectrometer module optical input and relays reflected light from the sample to the optical spectrometer module input. A similar embodiment to that shown in FIG. 17, but with a tungsten halogen lamp having a built-in lens may also be used for diffuse reflectance sampling.

Example Specific Embodiments

Figure 18:
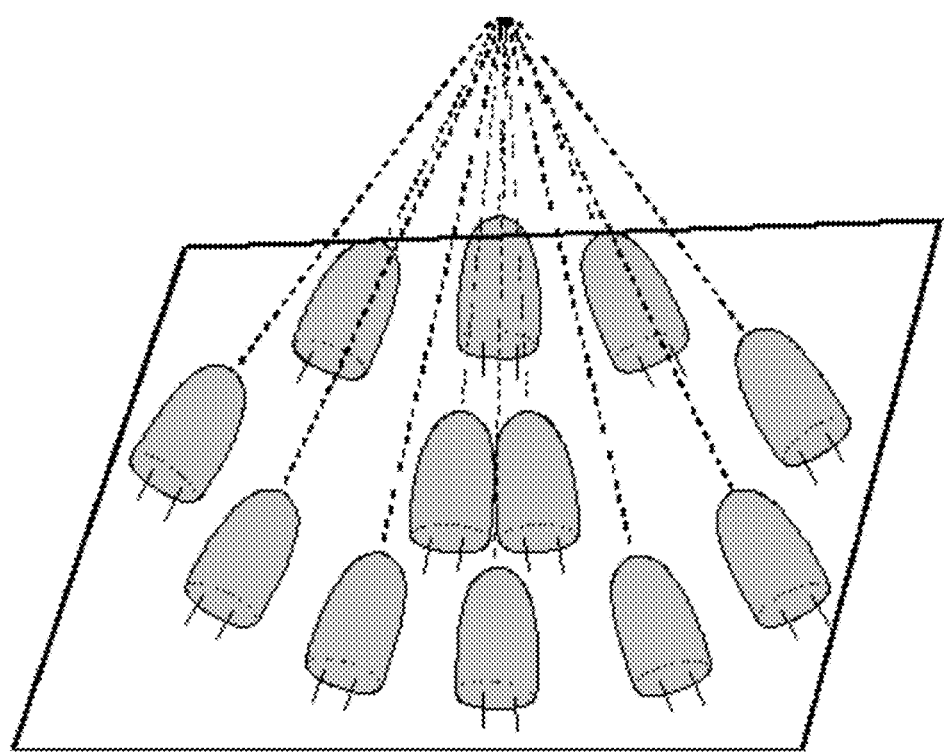
FIG. 18 is a three-dimensional drawing of a circular ring-shaped multi-LED array of 10 LEDs with two center LEDS adding as a second centered array.

One specific implementation of a system as shown in FIG. 3 is a multi-LED source NIR spectral analyzer system includes a light source constructed with ten different NIR LEDs arranged in a circular array with two additional LEDs mounted in the center of the array. The multi-LED light source provides continuous light emission over the 700-1050 nm wavelength range. The LEDs have center wavelengths at: 735, 760, 780, 800, 830, 870, 910, 940, 970, and 1020 nm. The ten LEDs at these wavelengths are mounted in a ring shaped array with optical axes mounted at an angle of 45° with respect to the normal to the plane of the LED ring. The 1020 nm LED is the weakest emitter, and the two additional LEDS are 1020 nm LEDs mounted in the center of the circular array with the angle of the optical axis of the two center-mounted LEDs about 7° to the ring normal. FIG. 18 shows LED alignment with the additional LEDs added in the center of the circular array. In this specific implementation, where there are ten 5 mm diameter LEDs mounted in the circular array, there is room for mounting up of 4 LEDs in the center of the circular array without extending the diameter of the outer LED circle. Extending the circle diameter for the ring array of 10 LEDs would lower the illumination intensity from these LEDs at the sample. The primary reason for addition of the duplicate wavelength LEDs that are mounted in the center of the primary array of 10 LEDs is to boost the illumination intensity for the LED types with the lowest power emission. It is preferred for the intensities at the different LED center wavelengths to be the same within a factor of 25. The LEDs are all clear plastic molded packages, with the molded-in lens axis pointing towards the center of the sample holder. A machined and polished aluminum cone reflector is used to provide concentration of the LED light on the sample.

The LEDs are powered with a 3.3V regulated modular wall mount DC power supply which connects to a printed circuit board on which the LEDs are mounted. The printed circuit board consists of an insulated epoxy/glass fiber board with a Cu metallization pattern on one side and with holes to receive the LED and resistor components. Current limiting resistors on the circuit board are each wired in series with each LED, and are used to lower the driving voltage and current for each LED to the appropriate value. The printed circuit conductor pattern on the back side of the circuit board has a circular ring conductor that connects to the + contacts of all of the LEDs and to the + terminal of the DC power supply. An L-shaped bus bar conductor near the outside edge of the circuit board connects to the − terminal of the DC power supply and to one side of the current limiting resistors. The other side of each resistor is connected to the − side of a different LED. The solder bond of the LED leads to the printed circuit board metallization secures the position of the LEDs.

Figure 19:
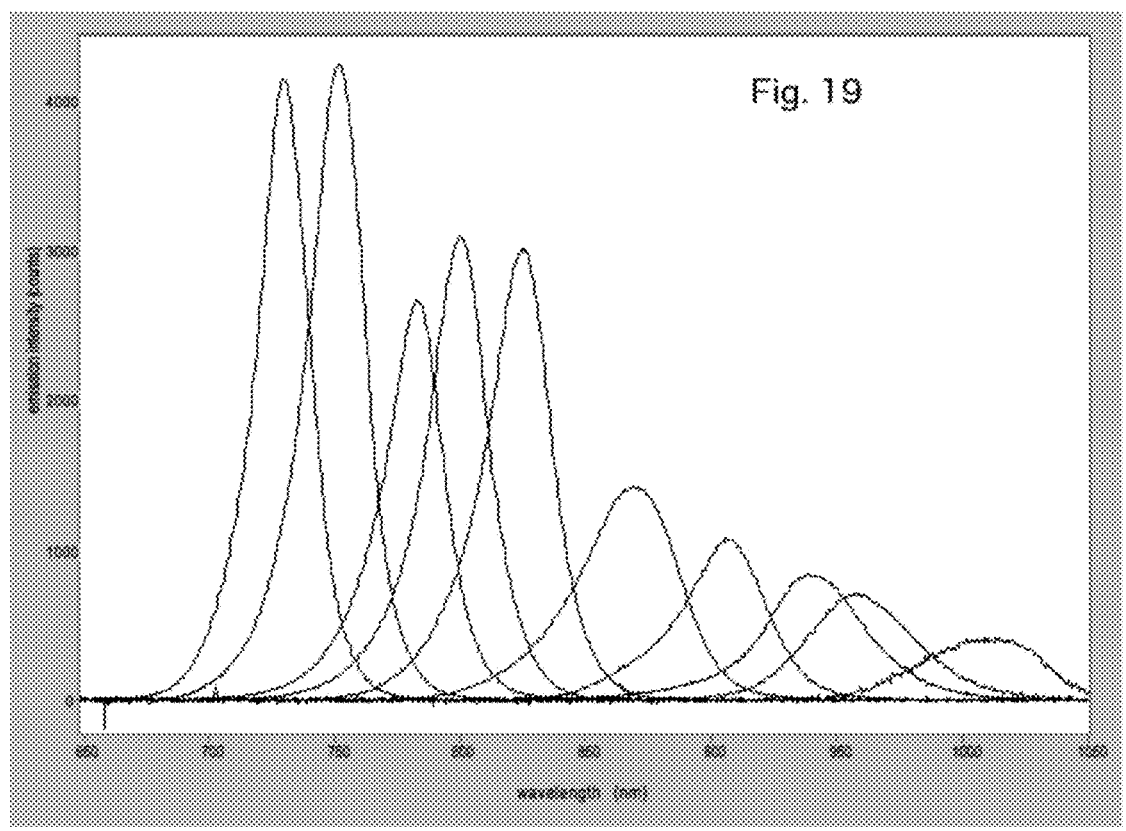
FIG. 19 is a spectrum showing the superimposed individual emission spectra of the 10 plastic encapsulated, 5 mm diameter package, LEDs used in the prototype analyzer system. The LEDs have emission peaks at approximately the following wavelengths: 735 nm, 760 nm 780 nm, 800 nm, 830 nm, 870 nm, 910 nm, 940 nm, 970 nm, and 1020 nm. The relative intensities in this composite spectrum are slightly different than those present in the final multi-LED light source used in the prototype analyzer system. This spectrum shows that the LEDs used in the prototype cover the whole spectral range from 700-1040 nm.
Figure 20:
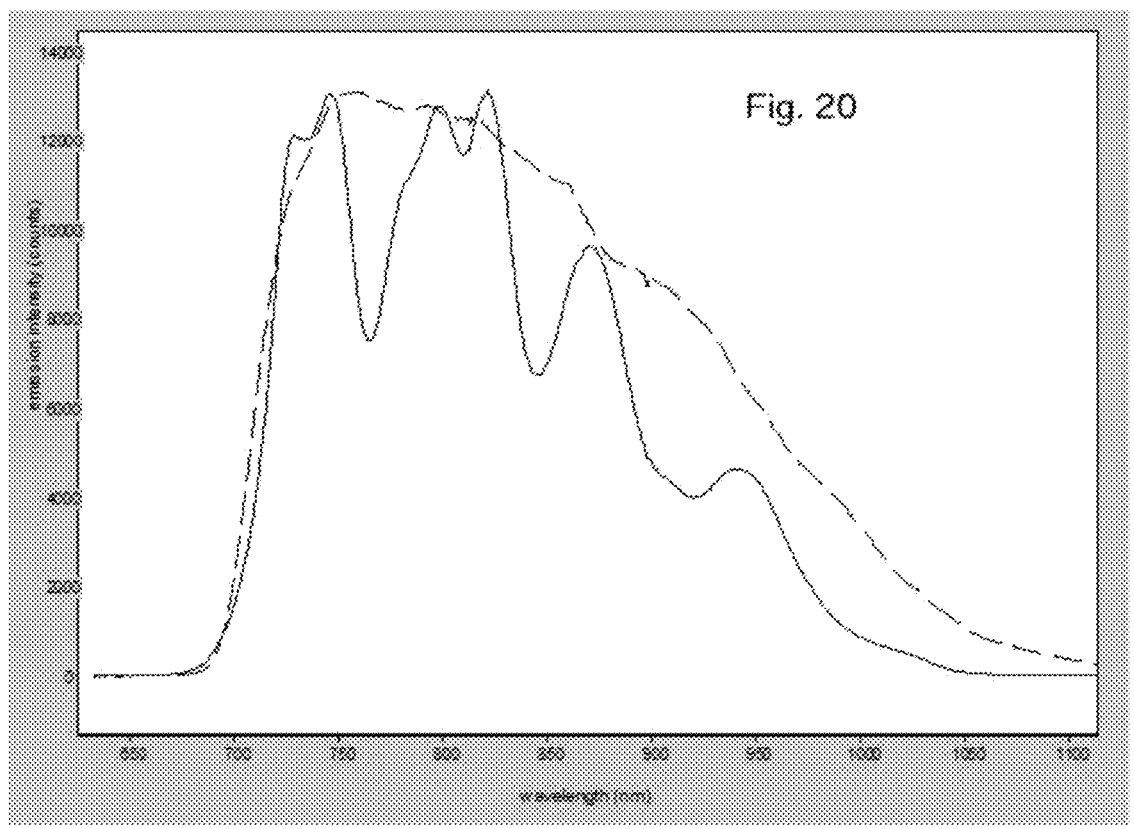
FIG. 20 is a comparison of the multi-LED source spectrum with a 9 W miniature tungsten halogen lamp spectrum. The multi-LED light source has a circular array of LEDs similar to that shown in FIG. 4. The spectra were measured through a 4.4 mm thick Spectralon attenuator placed in the sample holder so that the light intensity delivered to the spectrometer module was reduced to a level similar to that transmitted through a drug tablet. The upper curve (solid line) is the tungsten halogen lamp spectrum measured with 5 second integration time and with a 720 nm long pass filter and a 1050 nm short pass filter in the beam, and the lower curve (dashed line) is the multi-LED source (10 different LEDs) measured with a 10 second integration time (without any filters).

FIG. 19 shows a composite emission spectrum of all of the individual emission spectra of the 10 different LEDs used, with each LED spectrum measured separately. The spectra in FIG. 20 show the actual emission spectrum of the multi-LED light source (with LEDs all emitting simultaneously) together with a spectrum of a 9 W miniature tungsten halogen lamp of a type similar to those commonly used with miniature diffraction grating near-infrared and visible range spectrometers. The upper spectrum line is the tungsten halogen lamp and the lower spectrum line is the multi-LED light source. The two light source emission spectra shown in FIG. 20 are not plotted with the same vertical axis scale, and the emission of the tungsten halogen source is about 2.5 times stronger on average than the optical emission from the multi-LED source. The multi-LED light source is continuously driven with a 3.3V DC power supply and a set of current limiting resistors are used to lower the 3.3V supply voltage to the appropriate driving voltage for each LED. The total electrical power used by the multi-LED light source, including the current limiting resistors is 1.7 W, while the tungsten halogen source consumes 9 W.

Figure 21:
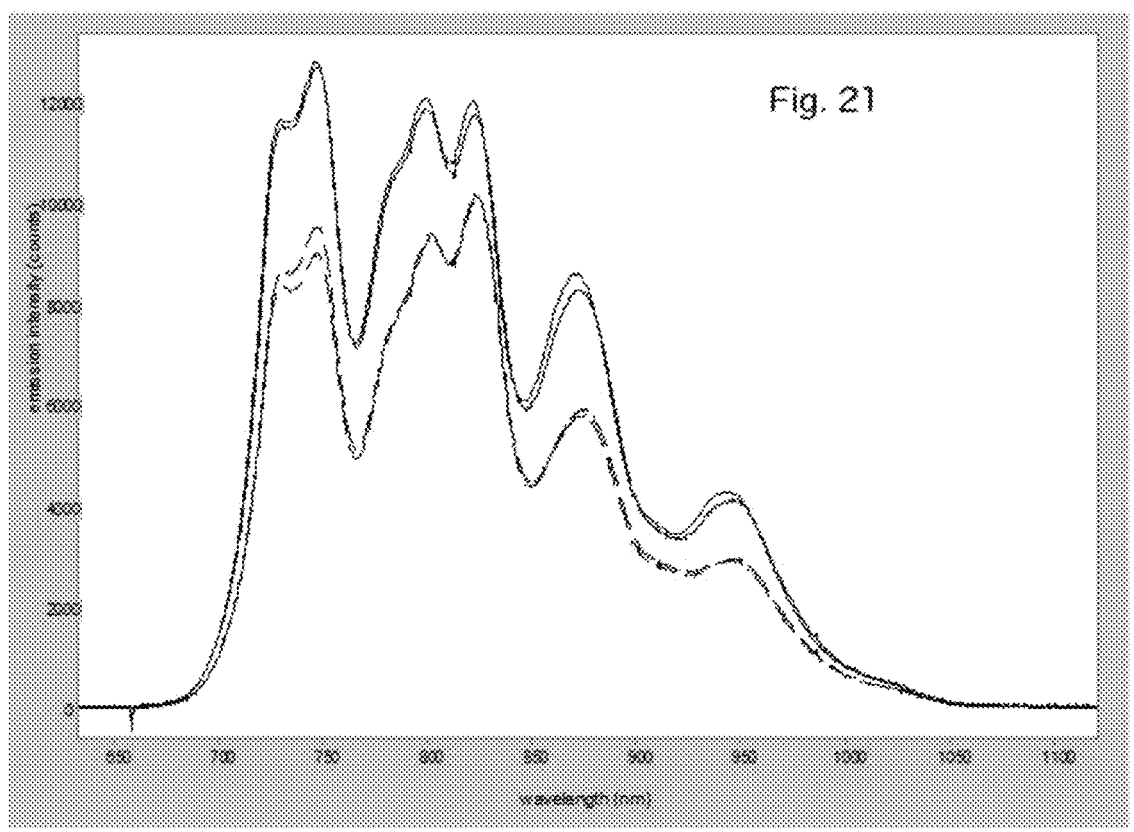
FIG. 21 is a comparison of two multi-LED light source emission spectra measured with the cone concentrator and two spectra measured without the cone concentrator. The upper curves (solid lines) are spectra with the concentrator and the lower curves (dashed lines) are spectra without the concentrator. The cone concentrator produces a 33% increase in LED illumination intensity relative to the LED array without the cone. Collection time is 10 seconds.

The increase in the multi-LED source intensity at the sample aperture that is produced by the cone concentrator is demonstrated by the emission spectra shown in FIG. 21. The upper spectra lines are measured with the cone concentrator while the lower spectra lines are measured without the cone concentrator. The cone concentrator produces a 33% increase in the LED source intensity at the sample aperture. Higher concentration factors may result from using a compound parabolic concentrator in place of the cone concentrator.

Spectral collection times with this system are 12 seconds or less. A Spectralon reference disk with a thickness of 4.4 mm is used as a reference sample to measure the light source reference spectrum for measurements of typical drug tablet samples such as ibuprofen and aspirin tablets.

Figure 22:
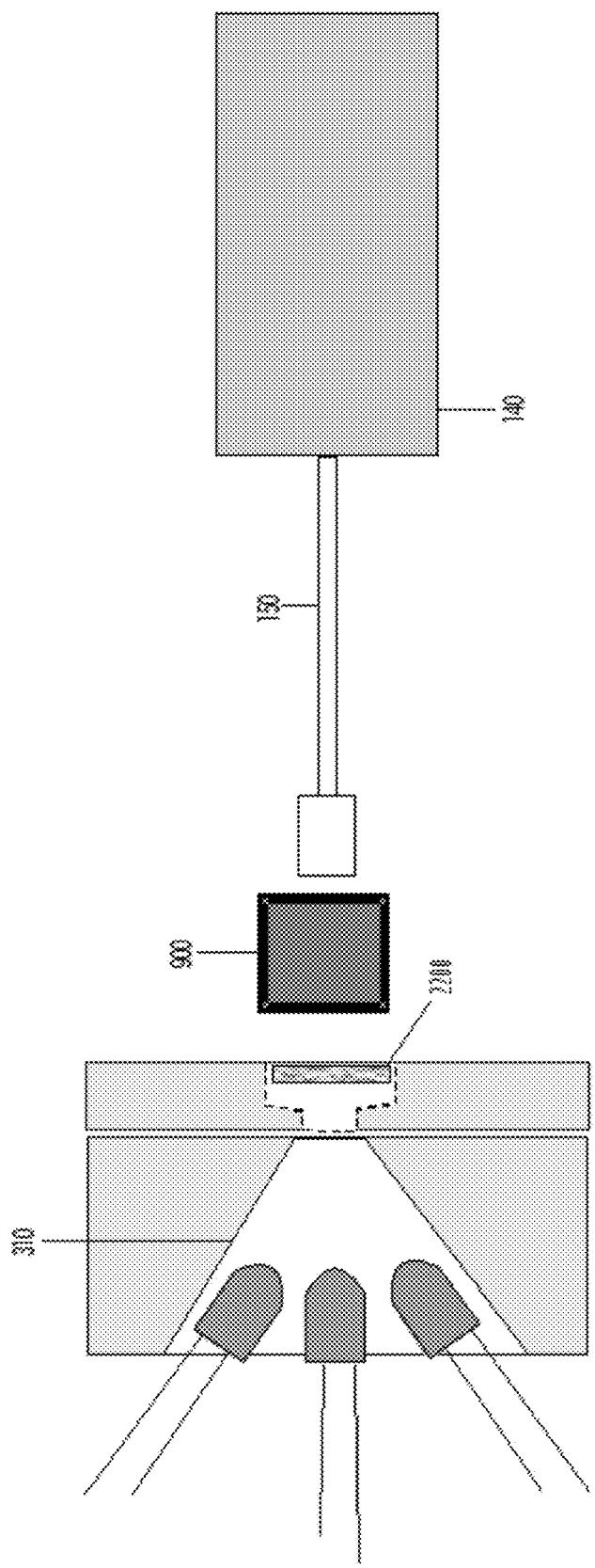
FIG. 22 shows a setup used for initial tests with the measurement of NIR spectra of liquid samples in a 1 cm pathlength cuvette.

For liquid samples, a 1 cm pathlength acrylic plastic cuvette is used. Reference spectra are measured with an empty cuvette. As shown in FIG. 22, all spectra of liquid samples are measured with a 1 mm thick Teflon diffuser 2200 mounted in the liquid sample holder insert and positioned between the LED light source and the cuvette. The diffuser increases the amount of LED light that passes through the cuvette and enters the spectrometer module input optical fiber. Without the diffuser, most of the light emitted from the ring shaped LED array that passes through the end of the cone concentrator is diverging at an angle of about 45° and misses the receiving fiber of the spectrometer module. The 45° diverging LED light is suitable for highly diffusing tablet and capsule samples but not for transparent liquid samples without using additional optics, such as the diffuser, to redirect the light. One important difference of the liquid medications relative to solid tablet or capsule medications is that the concentration of the active ingredients are at least 10 times lower in the liquid medication case. This concentration difference arises because the volume and mass of the normal dose for the liquid drugs is much larger (about 15 grams for liquid vs. about 0.5 grams for a tablet), but the amount of active ingredient per dose for liquid medication is still the same as for tablets for a given drug.

Figure 23:
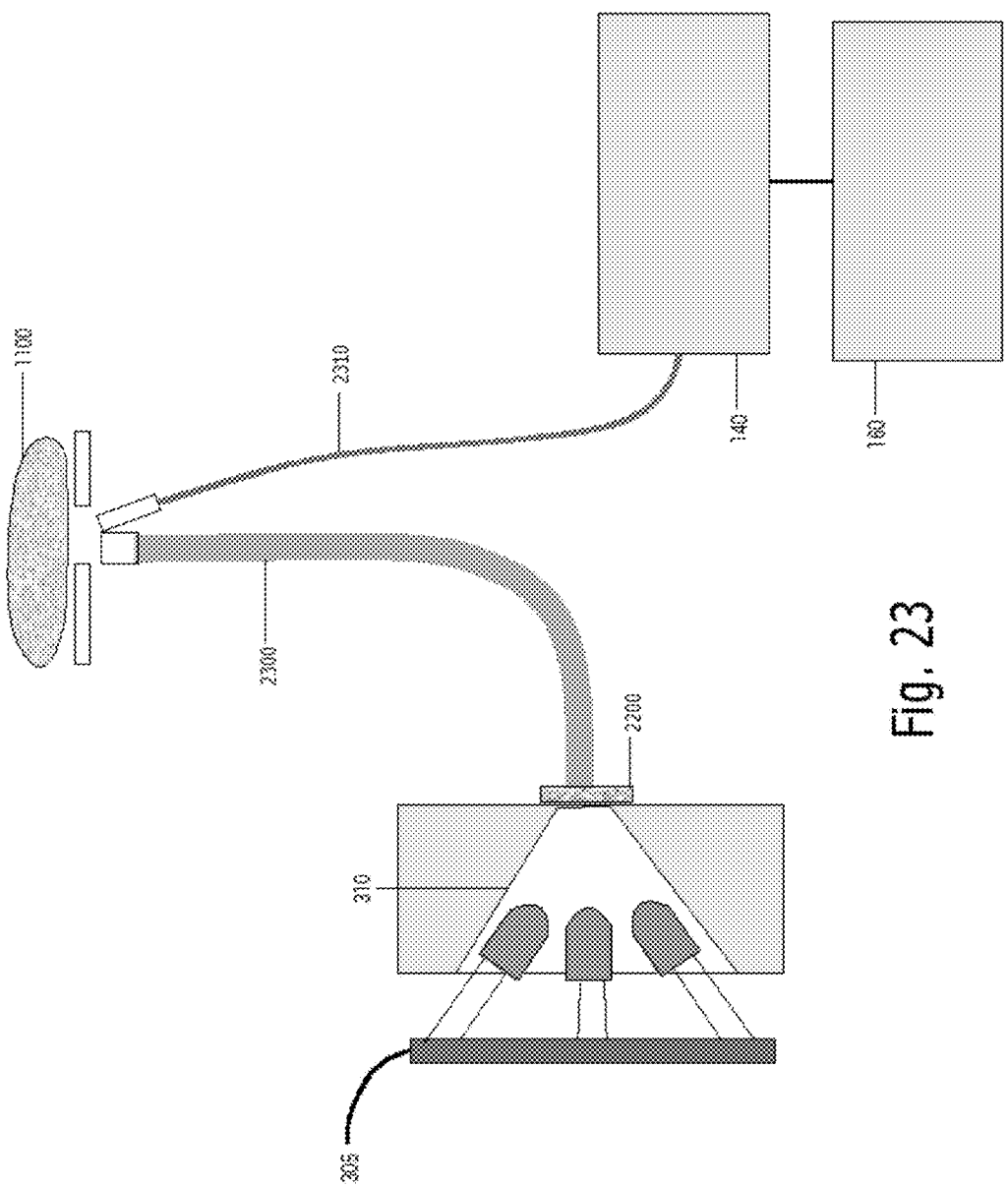
FIG. 23 is a diagram of experimental setup used to measure near-infrared diffuse reflection spectra of powder samples contained in plastic bags using a fiber-optic reflection probe.

FIG. 23 shows a system built for use with a reflection probe, and operates with a spectral collection time of 12 seconds. A fiber-optic reflection probe 2300 constructed from a 6 mm diameter fiber bundle relays the multi-LED source illumination to the sample, and a separate single fiber 2310 receives the reflected LED light from the sample and relayed it to the spectrometer module input. The 6 mm diameter illumination fiber bundle consists of about 7,800 fibers that are 50 μm in diameter. The single reflection receiving fiber is 400 μm in diameter. A 1 cm thick Spectralon plate provides a 100% reflectance standard to measure the light source reference spectrum. Similar to the setup for measuring liquid sample transmission spectra, a thin diffuser plate of 0.7 mm thick white Teflon is used to help homogenize the spatial wavelength distribution in the multi-LED light that enters the illumination fiber-optic bundle.

Figure 24:
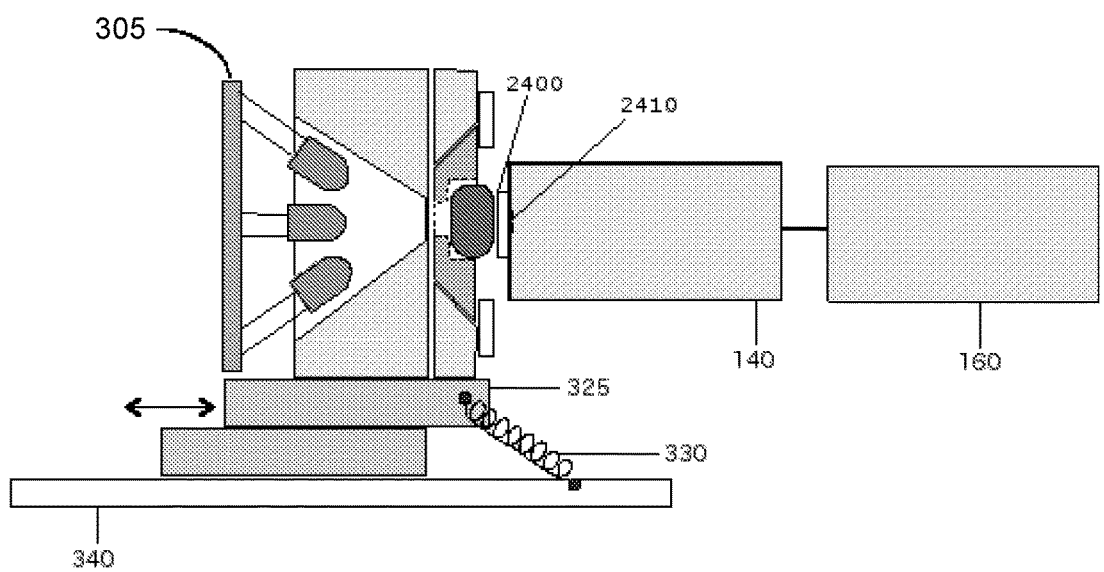
FIG. 24 is a diagram of an embodiment of the optical analyzer system operating without a fiber-optic input to the spectrometer module.
Figure 25:
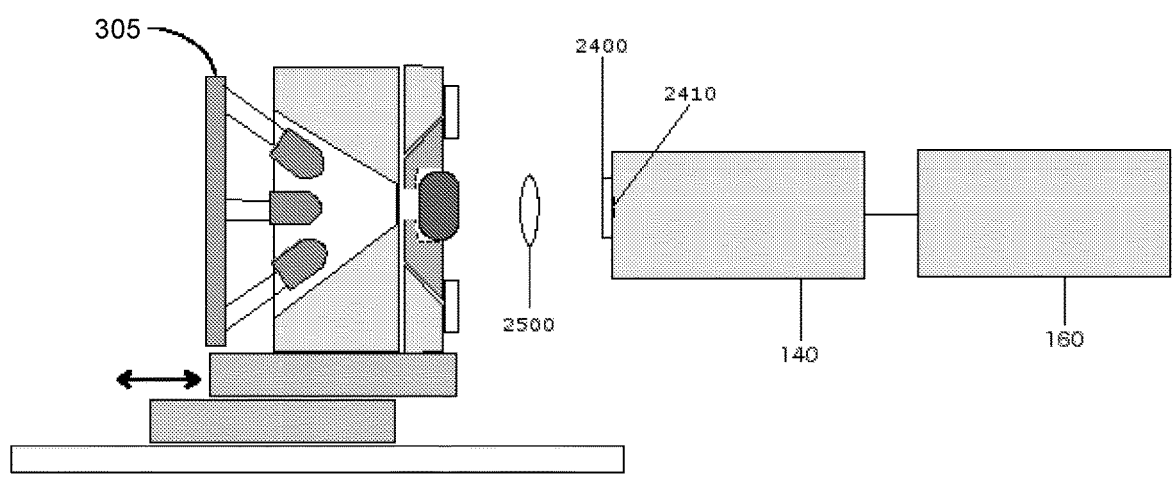
FIG. 25 is a diagram of an alternative embodiment of the optical analyzer system operating without a fiber optic input to the spectrometer module.

Although it is preferred to use an optical fiber to relay light from the sample to the spectrometer entrance slit, alternative embodiments may work without such fiber. FIGS. 24 and 25 show such embodiments. In both figures entrance window 2400, preferably a clear borosilicate glass or sapphire, protects entrance slit 2410 of spectrometer 110 and allows light to enter the spectrometer from the sample. As shown in FIG. 24, the sample holder may also be positioned in contact with the entrance window, where a spring 330 connecting translation stage 325 with base plate 340 is used to press the sample against the entrance window. FIG. 25 shows an embodiment where the sample is not in contact with the entrance window, where a glass or plastic relay lens 2500 is used to relay transmitted light from the sample to the spectrometer.

Using the preferred embodiment as shown in FIG. 3, four different types of drug tablets were measured. A Spectralon reference disk with a thickness of 4.4 mm was used as a reference sample to measure the light source reference spectrum for these tablet spectral measurements. FIG. 26 shows NIR absorbance spectra of 4 different types of drug tablets measured with the multi-LED light source, which show distinctly different spectral patterns. Shown are vitamin D (top spectrum line), Tylenol (upper middle spectrum line), Motrin ibuprofen (lower middle spectrum line), and Bayer aspirin (bottom spectrum line). Collection time was 12 seconds, except for the aspirin spectrum where a 6 second collection time was used.

Figure 27:
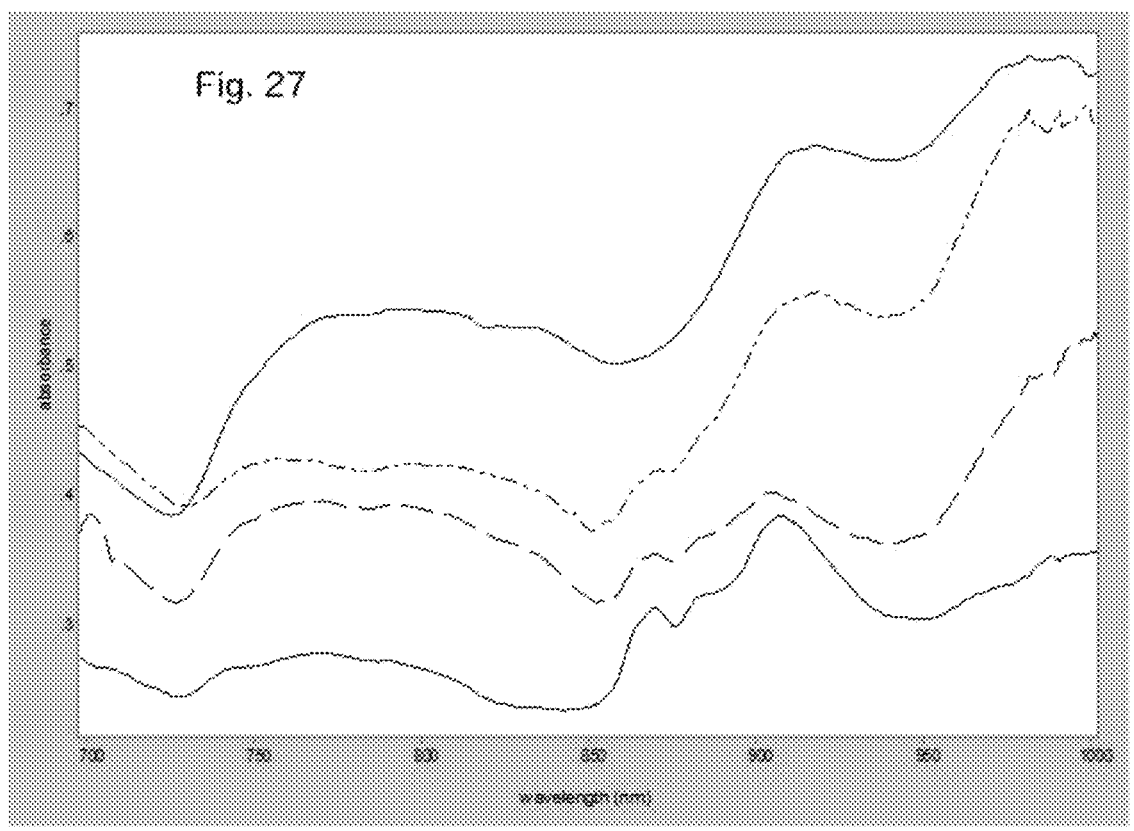
FIG. 27 shows measured spectra of powdered mixtures contained in drug capsules, with the upper curve (solid line) showing pure corn starch, the upper middle curve (dashed and dotted line) showing 25% quinine sulfate with 75% corn starch, the lower middle curve (dashed line) showing 50% quinine sulfate with 50% corn starch, and the bottom curve (solid line) showing pure quinine sulfate.

Using the capsule/tablet sample holder insert, short wavelength near-infrared transmission spectra of commercial drug capsules and also homemade test drug capsules were measured with the near-infrared analyzer with the multi-LED light source. A spectral collection time of 12 seconds was used for all measurements. The light source reference spectra were measured with the same Spectralon (compressed white Teflon powder) reference disk that was used for the tablet samples. Test capsule samples were produced by filling clear capsules with known two component mixtures of powders. The desired concentrations of the two component mixtures of quinine sulfate and corn starch were obtained by weighing out portions of each component with an electronic balance prior to mixing and filling the capsules. Size 1 clear gelatin capsules were used. FIG. 27 shows NIR absorbance spectra of capsules containing different mixtures of corn starch and quinine sulfate (anti-malarial drug). Shown are pure corn starch (upper spectrum line), pure quinine sulfate (bottom spectrum line), 50% quinine sulfate 50% corn starch, by weight (lower middle spectrum line), and 25% quinine sulfate with 75% corn starch (upper middle spectrum line). The spectra show that the 25% quinine sulfate can be detected and distinguished from 50% quinine and 0% quinine. Twenty-one point Savitzky-Golay smoothing was used.

Figure 28:
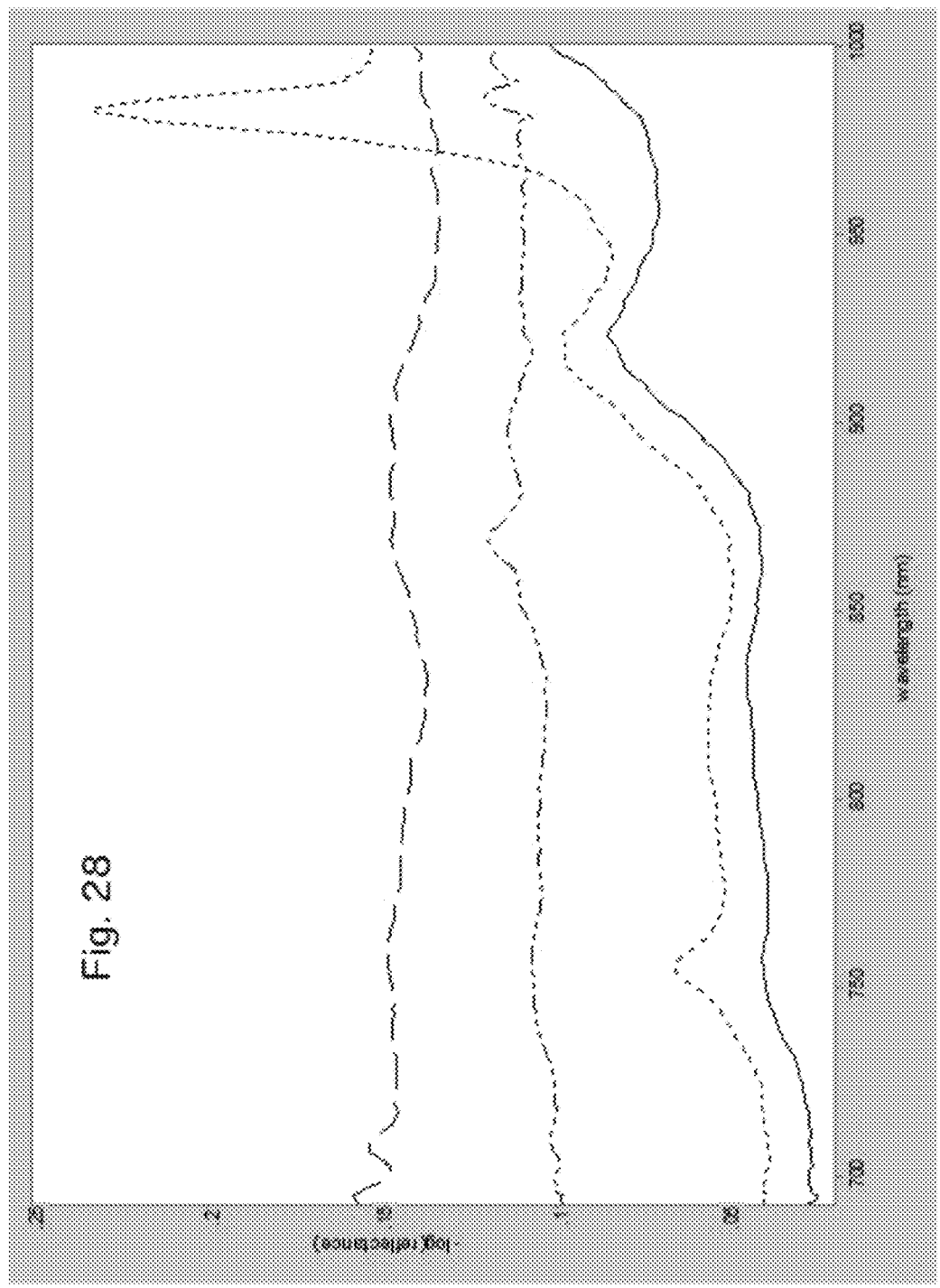
FIG. 28 shows measured reflectance spectra of powdered materials contained in clear polyethylene plastic bags, with the upper curve (dashed line) showing quinine sulfate, the upper middle curve (dashed and dotted line) showing acetaminophen, the lower middle curve (doted line) showing sucrose, and the bottom curve (solid line) showing glucose.

FIG. 28 shows examples of NIR diffuse reflection spectra of four different powdered materials contained in clear polyethylene plastic bags, where the spectra were measured from the outside of the plastic bag. The upper spectrum line is quinine sulfate, upper middle spectrum line is acetaminophen, lower middle spectrum line is sucrose, and bottom spectrum line is glucose. The spectra are offset in the y-axis to provide a clearer view of the spectra and the spectra were smoothed with a 21 point Savitsky-Golay smoothing routine. The spectral collection time was 12 seconds. These spectra were measured using a 9 W tungsten halogen lamp as the light source instead of the multi-LED light source.

It is to be understood that the above description is intended to be illustrative, and not restrictive. Many other embodiments will be apparent to those of skill in the art upon reviewing the above description. The scope of the disclosure should, therefore, be determined with reference to the appended claims, along with the full scope of equivalents to which such claims are entitled.

What is claimed is:

1. An optical analyzer system for identifying materials through transmission spectra analysis, the system consists of a light source and a set of non-light source components, wherein:

the light source consists of a circular monolithic array of light-emitting diode (LED) chips continuously powered with a DC power supply and covering either the 700-1100 or 900-1700 nm wavelength range; and the set of non-light source components comprises:

a sample holder system holding a sample of a drug tablet, or a drug capsule, or a capsule filled with powder, or a cuvette filled with liquid, or a piece of: plastic, carpet, plaster board, wood, cloth, mineral, or paper;

a sample aperture located between the LED chips and the sample holder system;

a solid waveguide with a polygonal cross section or an elliptically distorted polygonal cross section, the waveguide positioned between the LED chips and the sample aperture;

an optical encapsulant layer between the LED chips in the monolithic array and the waveguide, wherein the optical encapsulant layer contains an optical epoxy or an optical grade silicone sealant;

an optical spectrometer module operating in either of the 700-1100 nm spectral range or the 900-1700 nm spectral range, the optical spectrometer module positioned to receive light from the light source passing through the sample aperture and through an entire thickness of the sample within the sample holder system, the optical spectrometer system having:

an input slit;

a diffraction grating for wavelength dispersing;

a linear detector array with associated readout electronics to collect and integrate the signal from each detector element in the linear detector array, wherein the linear detector array has at least 128 detector elements, and wherein the detector elements respond within the wavelength range of 700-1100 nm or 900-1700 nm; and a spectral resolution of 10 nm or better; and a computer or microprocessor system interfaced with the optical spectrometer, wherein the computer or microprocessor system controls the collection of spectral data, storage of the collected spectral data, and performs processing of the spectral data using a qualitative multivariate calibration analysis algorithm.

* * * * *